US007973075B2

(12) United States Patent
Swanson et al.

(10) Patent No.: US 7,973,075 B2
(45) Date of Patent: Jul. 5, 2011

(54) KAINATE RECEPTOR-SELECTIVE EPIMERIC ANALOGS OF DYSIHERBAINE

(75) Inventors: Geoffrey T. Swanson, Oak Park, IL (US); Leanne Lash, Grandville, MI (US); Ryuichi Sakai, Hakodale (JP)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 12/243,281

(22) Filed: Oct. 1, 2008

(65) Prior Publication Data

US 2009/0118358 A1    May 7, 2009

Related U.S. Application Data

(60) Provisional application No. 60/976,889, filed on Oct. 2, 2007.

(51) Int. Cl.
  *A01N 43/16*   (2006.01)
  *A61K 31/35*   (2006.01)
  *C07D 311/00*  (2006.01)
(52) U.S. Cl. ...................................... 514/456; 549/396
(58) Field of Classification Search .................. None
  See application file for complete search history.

(56) References Cited

OTHER PUBLICATIONS

Greicius et al. "Presenile Dementia Syndrome: An Update on Taxonomy and Diagnosis". Journal of Neurol. Neurosurg. Psychiatry. 2002; 72:691-700.*
Gauthier et al. "Alzheimer's Disease: Current Knowledge, Management and Research". Can Med Assoc J., 1997; 157(8):1047-1052.*
Gasparini et al. "Peripheral Markers in Testing Pathophysiological Hypotheses and Diagnosing Alzheimer's Disease". FASEB J. 12, 1998:17-34.*
"Treatment". National Institute of Aging [Online]. [Retrieved Dec. 9, 2009]. Retrieved from the Internet: <URL:http://www.nia.nih.gov/Alzheimers/AlzheimersInformation/Treatment>.*
"Alzheimer's Disease and Related Dementias." Cecil's Textbook of Medicine (Twenty-First Edition, vol. 1). W.B. Saunders Company. 2000; pp. 2042-2045.*
Vippagunta et al. "Crystalline Solids". Advanced Drug Delivery Reviews. 2001; 48:3-26.*
Shoji et al. "Total Synthesis and Biological Evaluation of Neodysiherbaine A and Analogues". J. Org. Chem. 71(14); 2006:5208-5220.*
Konosu et al. "Beta-Lactam Antifungals.II. Enantiocontrolled Synthesis of (2R,5S)-2-Hydroxymethyl-1-carbapenam, the Carba-Analog of a Clavam Antifungal". Chem. Pharm. Bull. 39(11); 1991:2813-2818.*
Tamura et al., "Stereoselective Syntheses of 4-Hydroxy 4-Substituted Glutamic Acids", Journal of Organic Chemistry, 2005, 70:4569-4577.
Valgeirsson et al., "2-Arylureidobenzoic Acids: Selective Noncompetitive Antagonists for the Homomeric Kainate Receptor Subtype GluR5", Journal of Medical Chemistry, 2003, 46:5834-5843.
Valgeirsson et al., "Bioisosteric Modifications of 2-Arylureidobenzoic Acids: Selective Noncompetitive Antagonists for the Homomeric Kainate Receptor Subtype GluR5", Journal of Medical Chemistry, 2004, 47:6948-6957.
Valluru et al., "Ligand Binding is a Critical Requirement for Plasma Membrane Expression of Heteromeric Kainate Receptors", Journal of Biological Chemistry, Feb. 18, 2005, pp. 6085-6093, vol. 280, No. 7.
Vivithanaporn et al., "Intracellular Trafficking of KA2 Kainate Receptors Mediated by Interactions with Coatomer Protein Complex I (COPI) and 14-3-3 Chaperone Systems", Journal of Biological Chemistry, Jun. 2, 2006, pp. 15475-15484, vol. 281, No. 22.
Vivithanaporn et al., "Critical Roles for the M2-S2 Transduction Linker Domain in Kainate Receptor Assembly and Postassembly Trafficking", Journal of Neuroscience, Sep. 26, 2007, pp. 10423-10433, vol. 27, No. 39.
Weiss et al., "Pharmacological characterization of the Competitive GLU K5 Receptor Antagonist Decahydroisoquinoline LY466195 in Vitro and in Vivo", Journal of Pharmacology and Experimental Therapeutics, 206, pp. 772-781, vol. 318, No. 2.
Werner et al., "Cloning of a putative high-affinity kainate receptor expressed predominantly in hippocampal CA3 cells", Nature, Jun. 27, 1991, 351:742-744.
Yan et al., "A C-Terminal Determinant of GluR6 Kainate Receptor Trafficking", Journal of Neurosciences, Jan. 21, 2004, pp. 679-691, vol. 24, No. 3.
Alt et al., "Anxiolytic-like effects through a GLUK5 kainate receptor mechanism", Neuropharmacology, 2007, 52:1482-1487.
Ben-Ari et al., "Kainate, a double agent that generates seizures: two decades of progress", Trends in Neuroscience, 2000, 23(11):580-587.
Brickley et al., "CNQX increases GABA-mediated synaptic transmission in the cerebellum by an AMPA/kainate receptor-independent mechanism", Neuropharmacology, 2001, 41:730-736.
Bunch et al., "Subtype Selective Kainic Acid Receptor Agonists: Discovery and Approaches to Rational Design", Medicinal Research Reviews, 2009, pp. 3-28, vol. 29, No. 1.
Chen et al., "Pharmacological insights obtained from structure-function studies of ionotropic glutamate receptors", British Journal of Pharmacology, 2006, pp. 839-853, vol. 147.
Christensen et al., "In Vitro Characterization of 5-Carboxyl-2, 4-di-benzamido-benzoic Acid (NS3763), a Noncompetitive Antagonist of GLU K5 Receptors", Journal of Pharmacology and Experimental Therapeutics, 2004, pp. 1003-1010, vol. 309, No. 3.
Cohen et al., "Design, synthesis, and biological evaluation of a scaffold for iGluR ligands based on the structure of (–)-dysiherbaine", Bioorganic & Medicinal Chemistry Letters, 2006, 16:2189-2194.
Contractor et al., "Identification of the Kainate Receptor Subunits Underlying Modulation of Excitatory Synaptic Transmission in the CA3 Region of the Hippocampus", Journal of Neuroscience, Nov. 15, 2000, pp. 8269-8278, vol. 20, No. 22.
Contractor et al., "Kainate Receptors Are Involved in Short- and Long-Term Plasticity at Mossy Fiber Synapses in the Hippocampus", Neuron, Jan. 2001, pp. 209-216, vol. 29.

(Continued)

*Primary Examiner* — Leslie A Royds Draper
(74) *Attorney, Agent, or Firm* — Andrus, Sceales, Starke & Sawall, LLP

(57) ABSTRACT

Disclosed are compounds, pharmaceutical compositions, methods of treatment, and methods for selectively antagonizing a GluR5 receptor, a GluR6 receptor, or both receptors. The pharmaceutical compositions include and the methods utilize compounds that are analogs and stereoisomers of dysiherbaine and neodysiherbaine which have specificity for kainate receptors.

4 Claims, 15 Drawing Sheets

OTHER PUBLICATIONS

Contractor et al., "Loss of Kainate Receptor-Mediated Heterosynaptic Facilitation of Mossy-Fiber Synapses in KA2 Mice", Journal of Neurosciences, Jan. 15, 2003, pp. 422-429, vol. 23, No. 2.

Dolman et al., "Synthesis and Pharmacological Characterization of N3-Substituted Willardiine Derivatives: Role of the Substituent at the 5-Position of the Uracil Ring in the Development of Highly Potent and Selective GLUK5 Kainate Receptor Antagonists", Journal of Medicinal Chemistry, 2007, 50:1558-1570.

Epsztein et al., "Recurrent Mossy Fibers Establish Aberrant Kainate Receptor-Operated Synapses on Granule Cells from Epileptic Rats", Journal of Neuroscience, Sep. 7, 2005, pp. 8229-8239, vol. 25, No. 36.

Filla et al., "Ethyl (3S,4a,6S,8aR)-6-(4-Ethoxycarbonylimidazol-1-ylmethyl)decahydroisonquinoline-3-carboxylic Ester: A Prodrug of a GluR5 Kainate Receptor Antagonist Active in Two Animal Models of Acute Migraine", Journal of Medicinal Chemistry, 2002, 45:4383-4386.

Fisahn et al., "Distinct Roles for the Kainate Receptor Subunits GluR5 and GluR6 in Kainate-Induced Hippocampal Gamma Oscillations", Journal of Neuroscience, Oct. 27, 2004, pp. 9658-9668, vol. 24, No. 43.

Frisch, "Gaussian 09W Reference", (2004) Gaussian 03.

Herb et al., "The KA-2 Subunit fo Excitatory Amino Acid Receptors Shows Widespread Expression in Brain and Forms Ion Channels with Distantly Related Subunits", Neuron, Apr. 1992, 8:775-785.

Hollmann et al., "Cloned Glutamate Receptors", Annual Review of Neuroscience, 1994, 17:31-108.

Jones et al., "Development and Validation of a Genetic Algorithm for Flexible Docking", Journal of Molecular Biology, 1997, 267:727-748.

Kew et al., "Ionotropic and metabotropic glutamate receptor structure and pharmacology", Psychopharmacology, 2005, 179:4-29.

Lash et al., "Novel Analogs and Steroisomers of the Marine Toxin Neodysiherbaine with Specificity for Kainate Receptors", Journal of Pharmacological and Experimental Therapeutics, Feb. 2008, pp. 484-496, vol. 324, No. 2.

Lerma et al., "Molecular Physiology of Kainate Receptors", Physiological Reviews, Jul. 2001, 81(3):971-998.

Lerma, "Kainate Receptor Physiology", Current Opinion in Pharmacology, 2006, 6:89-97.

Mayer, "Crystal Structures of the GluR5 and GluR6 Ligand Binding Cores: Molecular Mechanisms Underlying Kainate Receptor Selectivity", Neuron, Feb. 17, 2005, pp. 539-552, vol. 45.

Minei, "Effects of a New Excitotoxic Amino Acid, Dysiherbaine, on Cultured Muller Cells", Japanese Journal of Ophthalmology, 2002, 46:153-159.

Mulle et al., "Altered synaptic physiology and reduced susceptibility to kainate-induced seizures in GluR6-deficient mice", Nature, Apr. 1998, 392:601-605.

Nanao et al., "Structure of the kainate receptor subunit GluR6 agonist-binding domain complexed with domoic acid", PNAS, Feb. 1, 2005, pp. 1708-1713, vol. 102, No. 5.

Naur et al., "Crystal structure of the kainate receptor GluR5 ligand-binding core in complex with (s)-glutamate", FEBS Letters, 2005, 579:1154-1160.

Paternain et al., "Comparative Antagonism of Kainate-activated Kainate and AMPA Receptors in Hippocampal Neurons", European Journal of Neuroscience, 1996, 8:2129-2136.

Pentikainen et al., "Subtype selectivity and flexibility of ionotropic glutamate receptors upon antagonist ligand binding", Organic & Biomolecular Chemistry, 2006, pp. 1058-1070, vol. 4.

Pentikainen et al., "Cooperative symmetric to asymmetric conformational transition of the apo-form of scavenger decapping enzyme revealed by simulations", Proteins, 2007, 498-508.

Phillips et al., "Total Synthesis of Dysiherbaine", Journal of Organic Chemistry, 2002, 67:3194-3201.

Phillips et al., "Scalable Molecular Dynamics with NAMD", Journal of Computational Chemistry, Dec. 2005, pp. 1781-1802, vol. 26, No. 16.

Pinheiro et al., "Kainate Receptors", Cell and Tissue Research, 2006, 326:457-482.

Ren et al., "Multiple Trafficking Signals Regulate Kainate Receptor KA2 Subunit Surface Expression", Journal of Neuroscience, Jul. 23, 2003, pp. 6608-6616, vol. 23, No. 16.

Sakai et al., "Dysiherbaine: A New Neurotoxic Amino Acid from the Micronesian Marine Sponge *Dysidea herbacea*", Journal of the American Chemical Society, 1997, 119:4112-4116.

Sakai et al., "Isolation, Structure Determination, and Synthesis of Neodysiherbaine A, a New Excitatory Amino Acid from a Marine Sponge", Organic Letters, 2001, pp. 1479-1482, vol. 3, No. 10.

Sakai et al., "Pharmacological Properties of the Potent Epileptogenic Amino Acid Dysiherbaine, a Novel Glutamate Receptor Agonist Isolated from the marine Sponge *Dysidea herbacea*", Journal of Pharmacology and Experimental Therapeutics, 2001, pp. 650-658, vol. 296, No. 2.

Sanders et al., "Divergent Pharmacological Activity of Novel Marine-Derived Excitatory Amino Acids on glutamate Receptors", Journal of Pharmacology and Experimental Therapeutics, 2005, pp. 1068-1078, vol. 314, No. 3.

Sanders et al., "Determination of Binding Site Residues Responsible for the Subunit Selectivity of Novel Marine-Derived Compounds on Kainate Receptors", Molecular Pharmacology, 2006, pp. 1849-1860, vol. 69, No. 6.

Sasaki et al., "Synthesis and Biological Activity of Dysiherbaine Model Compound", Tetrahedron Letters, 1999, 40:3195-3198.

Sasaki et al., "Design, total synthesis, and biological evaluation of neodysiherbaine A derivative as potential probes", Bioorganic and Medicinal Chemistry Letters, 2006, 16:5784-5787.

Sasaki et al., "Rapid and Efficient Synthesis of Dysiherbaine and Analogues to Explore Structure-Activity Relationships", Journal of Organic Chemistry, 2008, 73:264-273.

Schiffer et al., "Unequal Expression of Allelic Kainate Receptor GluR7 mRNAs in Human Brains", Journal of Neuroscience, Dec. 15, 2000, pp. 9025-9033, vol. 20, No. 24.

Smolders et al., "Antagonists of GLUK5-containing kainate receptors prevent pilocarpine-induced limbic seizures", Nature Neuroscience, Aug. 2002, 5(8):796-804.

Srivastava et al., "Rapid enhancement of two-step wiring plasticity by estrogen and NMDA receptor activity", PNAS, Sep. 23, 2008, pp. 14650-14655, vol. 105, No. 38.

Swanson et al., "Identification of Amino Acid Residues that Control Functional Behavior in GluR5 and GluR6 Kainate Receptors", Neuron, Oct. 1997, 19:913-926.

Swanson et al., "Kainate Receptors Exhibit Differential Sensitivities to (S)-5-Iodowillariine", Molecular Pharmacology, 1998, pp. 942-949, vol. 53.

Swanson et al., "Differential Activcation of Individual Subunits in Heteromeric Kainate Receptors", Neuron, May 16, 2002, pp. 589-598, vol. 34.

Takahashi et al., "A highly sterocontrolled total synthesis of dysiherbaine", Chemical Communications, 2007, 4158-4160.

* cited by examiner

8-deoxy-neodysiherbaine

9-deoxy-neodysiherbaine

*4-epi-neodysiherbaine*

*8-epi-neodysiherbaine*

*9-epi-neodysiherbaine*

*8,9-epi-neodysiherbaine*

8-epi-neoDH
GluR5-2a Receptors

8,9-epi-neoDH
GluR5-2a Receptors

4-epi-neoDH

Group 1 - Deoxy Analogs

8-deoxy-neoDH        9-deoxy-neoDH        neoDH        MSVIII-19

Group 2 - C8/C9 Epimer Analogs

8-epi-neoDH        9-F-8-epi-neoDH        9-epi-neoDH        8,9-epi-neoDH

Group 3 - C2/C4 Epimer Analogs

2,4-epi-neoDH        4-epi-neoDH

A GluR5-2a receptors

B GluR6a receptors

KAINATE RECEPTOR-SELECTIVE EPIMERIC ANALOGS OF DYSIHERBAINE

CROSS-REFERENCE TO RELATED PATENT APPLICATIONS

This application claims the benefit under 35 U.S.C. §119 (e) to U.S. Provisional Patent Application No. 60/976,889, filed on Oct. 2, 2007, the content of which is incorporated herein by reference in its entirety.

STATEMENT REGARDING FEDERALLY SPONSORED RESEARCH OR DEVELOPMENT

This invention was made with U.S. Government Support under grant no. R01NS044322 awarded by the National Institute of Neurological Disorders and Stroke. The U.S. Government has certain rights in the invention.

BACKGROUND

Glutamate receptors are the primary mediators of excitatory synaptic transmission in the central nervous system. Kainate receptors (KARs), a member of the ionotropic glutamate receptor family, have roles in brain physiology and pathology that are poorly characterized. Natural source compounds have been useful tools for identification and characterization of these receptors and their role in many processes. In particular, dysiherbaine (DH) has been isolated from the Micronesian sponge *Dysidea herbacea* and has been found to be a potent kainate receptor agonist and subsequently, a powerful convulsant (Sakai et al., J. AM. CHEM. SOC. 1997; 119: 4112-16; and Sakai et al., JPET 2001; 296:650-8)

Dysiherbaine is a structurally unique KAR ligand, with a glutamate backbone connected to a rigid ring structure containing a methylamine substituent at the C8 ring position and a hydroxyl group at the C9 ring position (Sasaki et al., Tetra. Lett. 1999; 40:3195-8). This unique chemical structure, along with the distinct pharmacological profile of DH, suggests it could be useful as a template for the generation of molecules with unique pharmacological profiles that target KARs. Toward that end, neodysiherbaine (neoDH) and MSVIII-19, a natural and synthetic analog, respectively, were characterized (Sanders et al., 2005; JPET; 314:1068-78). The structure of these analogs differs slightly from the parent compound DH; neoDH has a hydroxyl group replacing the C8 methylamine of DH and MSVIII-19 lacks both the C8 and C9 functional groups. However, these slight structural variations distinctly after the pharmacological profiles of these analogs.

Here, we further study the role that critical substituents, and the spatial orientation of these substituents, have on pharmacological activity for dysiherbaine and its analogs and derivatives. A second generation of DH analogs was synthesized based upon information obtained from the characterization of neoDH and MSVIII-19. These epimer analogs altar the orientation of substituents at several critical positions of the molecule and exhibit selective antagonist properties for the glutamate receptors GluR5 and GluR6 relative to other glutamate receptors.

SUMMARY

Disclosed are compounds, pharmaceutical compositions, methods of treatment, and methods for selectively antagonizing a kainate receptor such as a GluR5 receptor, a GluR6 receptor, or both receptors. The disclosed compounds include stereoisomers of dysiherbaine, neodysiherbaine, and analogs and derivatives thereof. In particular, the pharmaceutical compositions may include and the methods may utilize a compound having a formula ("Formula I"):

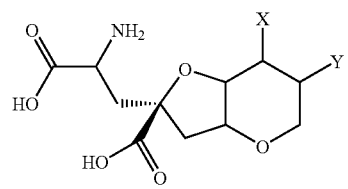

or a salt, ester, amide, or solvate thereof, wherein X and Y may be the same or different and are selected from a group consisting of H, OH, $NH_2$ (optionally substituted with $C_{1-6}$ alkyl such as NHMe), or halide (e.g., fluoro, chloro, bromo, or iodo).

Preferably, the compound has a formula ("Formula II"):

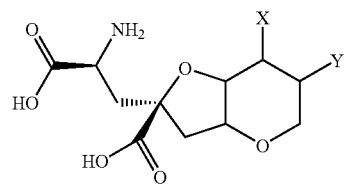

where X and Y are as defined above.

More preferably, X and Y are OH and the compound has a formula ("Formula III") otherwise referred to as "2,4-epi-neodysiherbaine":

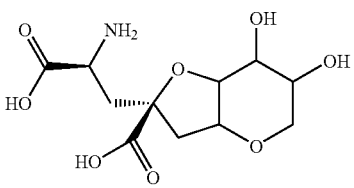

In some embodiments, the compound may have a formula ("Formula IV") otherwise referred to as "4-epi-neodysiherbaine":

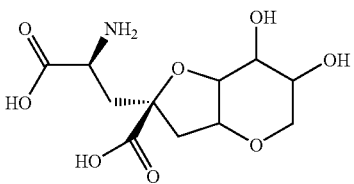

The pharmaceutical composition may be suitable for use in methods of treating neurological disorders or neurodegenerative diseases. The compounds may be utilized in methods for selectively antagonizing one or more kainate receptors such as GluR5, GluR6, or the compounds may be utilized in methods for selectively antagonizing both GluR5 and GluR6.

DETAILED DESCRIPTION

Figure 1:
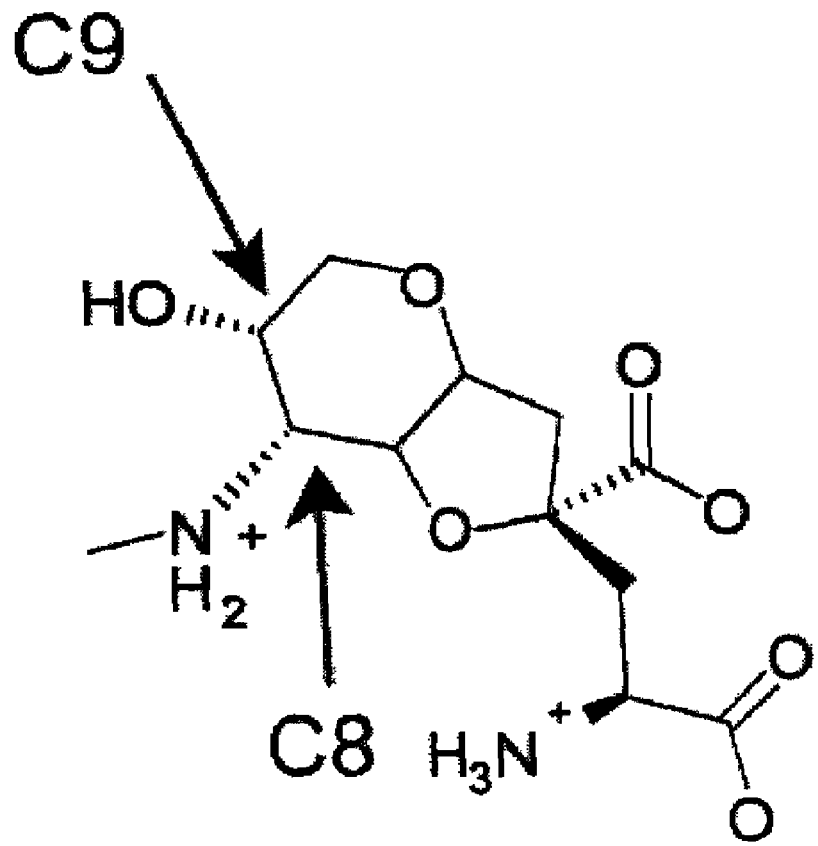
FIG. 1 provides the structure for dysiherbaine and illustrates the positions of the C8 and C9 carbon atoms.

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus≦10% of the particular term and "substantially" and "significantly" will mean plus or minus>10% of the particular term.

As used herein, the terms "include" and "including" have the same meaning as the terms "comprise" and "comprising."

The terms "patient" and "subject" may be used interchangeably herein. A patient may be a human patient. A patient may refer to a human patient having or at risk for acquiring a neurological disorder or a neurodegenerative disease.

As used herein, "iGluRs" refers to ionotropic glutamate receptors which may be further classified as "NMDA receptors" and "non-NMDA receptors." "NMDA receptors" refers to receptors for N-methyl-D-aspartic acid. The non-NMDA receptors include "AMPA receptors" and "KA receptors" (or kainate receptors).

As used herein, "AMPA receptors" refers to receptors for α-amino-3-hydroxy-5-methyl-4-isoxazolepropionic acid and includes GluR1-4. "GluR1," "GluR2," "GluR3," and "GluR4" refer to AMPA glutamate receptor subtypes 1-4, respectively.

As used herein, "KA receptors" refers to receptors for kainic acid and includes the receptors GluR5, GluR6, GluR7, KA1, and KA2. As used herein, "GluR5 receptor" refers to kainate glutamate receptor subtype 5; "GluR6 receptor" refers to kainate glutamate receptor subtype 6; "GluR7 receptor" refers to kainate glutamate receptor subtype 7; "KA1 receptor" refers to kainic acid receptor subtype 1; and "KA2 receptor" refers to the kainic acid receptor subtype 2.

As used herein, "selectively antagonizing" is meant to refer to include antagonism resulting from selective binding of the compound to GluR5 receptors, GluR6 receptors, (or both GluR5 receptors and GluR6 receptors), relative to other non-NMDA receptors (e.g., relative to the receptors GluR1, GluR2, GluR3, GluR4, GluR7, KA1, KA2, or combinations thereof). For example, the compound may have a binding affinity for GluR5 receptor, for GluR6 receptor, (or a binding affinity for both GluR5 receptor and GluR6 receptor) that is at least 3-fold greater (or at least 5-fold greater, at least 10-fold greater, at least 20-fold greater, at least 50-fold greater, or at least 100-fold greater) than a binding affinity for other non-NMDA receptors (e.g., than a binding affinity for any of the receptors GluR1, GluR2, GluR3, GluR4, GluR7, KA1, and KA2).

In another example, the compound may displace kainate (e.g., [$^3$H]kainate) from GluR5 receptors, from GluR6 receptors, or from both GluR5 receptors and GluR6 receptors, more efficiently than from other kainate receptors (e.g., GluR7, KA1, and KA2). In some embodiments, a selective antagonist may have a $K_i$ value ($K_i$=IC$_{50}$/(1+[radioligand]/$K_d$) for GluR5 receptor, a $K_i$ value for GluR6 receptor, (or a $K_i$ value for both GluR5 receptor and GluR6 receptor), which is less than about 20 µM (preferably less than about 10 µM, more preferably less than about 5 µM, most preferably less than about 1 µM); and the selective antagonist may have a $K_i$ value for another kainate receptor (e.g., GluR7, KA1, or KA2) or an AMPA receptor (e.g., GluR1, GluR2, GluR3, or GluR4) that is greater than about 20 µM, (preferably greater than about 30 µM, more preferably greater than about 100 µM). For example, a selective antagonist for GluR5 receptor and GluR6 receptor may have: (i) a $K_i$ value for GluR5 receptor of less than about 10 µM; (ii) a $K_i$ value for GluR6 receptor of less than about 10 µM; and (iii) $K_i$ values for GluR7, KA2, GluR1, and GluR2 receptors which are greater than about 30 µM, and preferably greater than about 100 µM.

The disclosed compounds include stereoisomers of dysiherbaine (DH), neodysiherbaine (neoDH), analogs, and derivatives thereof. Dysiherbaine (DH) has the formula:

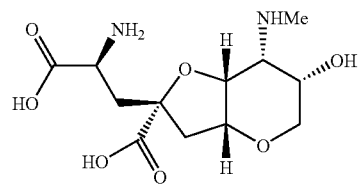

Neodysiherbaine (neoDH) has the formula:

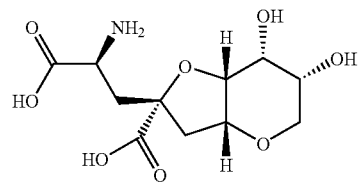

Analogs and derivatives of dysiherbaine and neodysiherbaine may include, for example, a compound having a formula ("Formula I"):

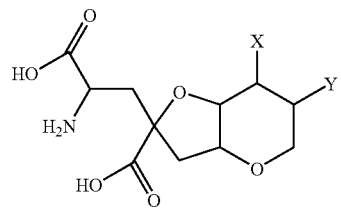

or a salt, ester, amide, or solvate thereof, wherein X and Y may be the same or different and are selected from a group consisting of H, OH, NH$_2$ (optionally substituted with C$_{1-6}$ alkyl such as NHMe), or halide (e.g., fluoro, chloro, bromo, or iodo). Preferably, analogs and derivatives of dysiherbaine and neodysiherbaine selectively antagonize the GluR5 receptor, the GluR6 receptor, or both receptors.

Analogs and derivatives of dysiherbaine and neodysiherbaine may include 8-deoxy analogs and 9-deoxy analogs, for example, any of the following compounds:

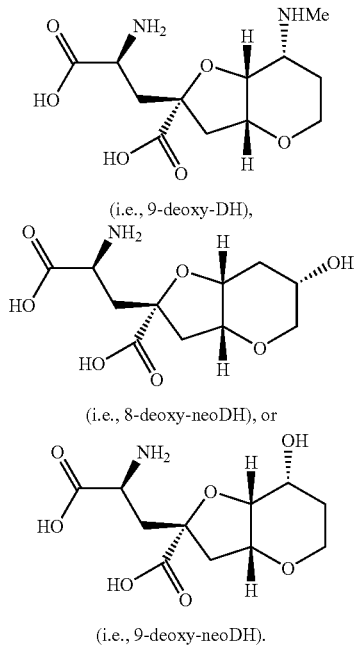

(i.e., 9-deoxy-DH), (i.e., 8-deoxy-neoDH), or (i.e., 9-deoxy-neoDH).

Stereoisomers of dysiherbaine and neodysiherbaine may include epimers. In some embodiments, epimers may include 2-epimers, 4-epimers, or 2,4-epimers, for example, a compound having one of the formulae:

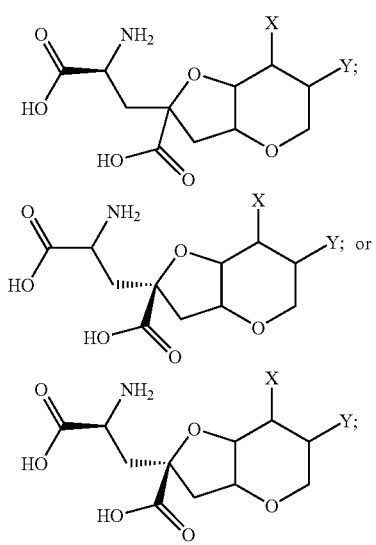

or a salt, ester, amide, or solvate thereof, wherein X and Y may be the same or different and are selected from a group consisting of H, OH, $NH_2$ (optionally substituted with $C_{1-6}$ alkyl such as NHMe), or halide (e.g., fluoro, chloro, bromo, or iodo). Preferably, epimers selectively antagonize the GluR5 receptor, the GluR6 receptor, or both receptors. In some embodiments, epimers have one of the following formulae:

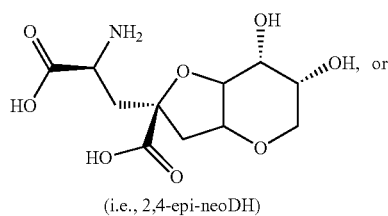

(i.e., 2,4-epi-neoDH)

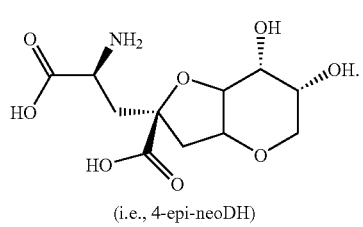

(i.e., 4-epi-neoDH)

The compounds disclosed herein can be prepared, for example, using the synthetic scheme described in Sasaki et al., "Synthesis and Biological Activity of Dysiherbaine Model Compound," *Tetrahedron Letters*, 40:31.95-3198 (1999), and Sakai et al., "Isolation, Structure Determination, and Synthesis of Neodysiherbaine A, a New Excitatory Amino Acid from a Marine Sponge, *Organic Letters*, 3(10): 1479-1482 (2001); which are hereby incorporated by reference. Other synthesis methods for dysiherbaine and neodysiherbaine compounds, analogs, and derivatives thereof are disclosed in Cohen et al., "Synthesis of the dysiherbaine tetrahydropyran core employing a tethered aminohydroxylation reaction," Tetrahedron Lett. 2007 Apr. 2; 48(14): 2533-2536; Sasaki et al., "Total synthesis of (−)-dysiherbaine, a novel neuroexcitotoxic amino acid," Tetrahedron Lett. 2000 May 21; 41(20): 3923-3926; and Sasaki et al., "Rapid and efficient synthesis of dysiherbaine and analogues to explore structure activity relationships," J. Org. Chem. 2008; 73(1): 264-273; which are hereby incorporated by reference.

It will be appreciated that the compounds disclosed herein (e.g., compounds of Formulas I, II, III, and IV) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers of dysiherbaine, neodysiherbaine, or analogs or derivatives thereof are contemplated herein (e.g., a composition comprising at least about 90%, 95%, or 99% pure stereoisomer, epimer, or enantiomer such as 2,4-epi-neoDH or 4-epi-neoDH.)

As used herein, formulae which do not specify the orientation at one or more chiral centers are meant to encompass all orientations and mixtures thereof. Illustratively, the compounds of Formula I are meant to include, but are not limited to compounds having the following formulae:

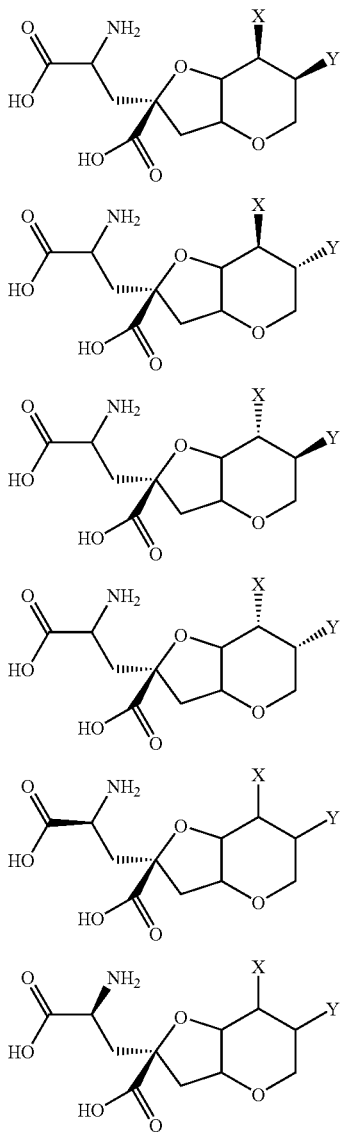

in which X and Y are defined as above. Compounds of Formula I are meant to include, but are not limited to DH, neoDH, 4-epi-neoDH, and 2,4-epi-neoDH.

As indicated above, pharmaceutically acceptable salts of the compounds are contemplated and also may be utilized in the disclosed methods. For example, the carboxylic acid groups of the disclosed compounds may be deprotonated and the amino groups of the disclosed compounds may be protonated. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-. 1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counter-ion forming a part of any salt of a compound disclosed herein is usually not of a critical nature, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

It will be further appreciated that the disclosed compounds can be in equilibrium with various inner salts, such as those represented by the following formulae:

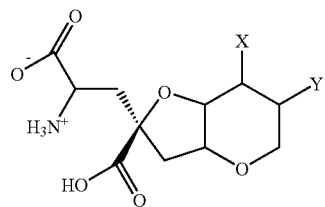

-continued

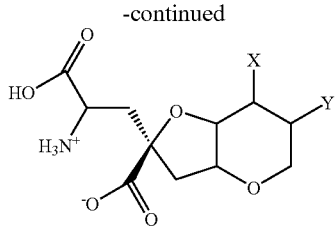

where X and Y are as defined above, and that all of these and other inner salts are meant to be encompassed by the disclosed compounds and formulae.

The methods disclosed herein may be practiced in vitro or in vivo. More particularly, the methods disclosed herein may be used in vivo to treat neuropathic pain and other forms of aberrant nociception as well as migraines, and epilepsy, and other neurological disorders. In the case where the methods disclosed herein are carried out in vivo, for example, where the GluR5 receptors or GluR6 receptors are present in a human subject, contacting can be carried out by administering a therapeutically effective amount of the compound to the human subject, for example, by directly injecting the compound into the subject in the vicinity of the GluR5 receptors or GluR6 receptors to be contacted or by other suitable means of administration. Details with regard to this and other methods for administering compounds in accordance with the methods disclosed herein are further described below. Also disclosed are methods of treating a neurological disorder or a neurodegenerative disease in a subject. The methods may include administering to the subject a tetrahydrofuro[3,2-b]tetrahydropyran antagonist that is selective for the GluR5 receptor, the GluR6 receptor, or both receptors.

As used herein, "selective tetrahydrofuro[3,2-b]tetrahydropyran antagonist" is meant to refer to compounds that are both (i) tetrahydrofuro[3,2-b]tetrahydropyrans and (ii) selective antagonists (e.g., a selective antagonist for the GluR5 receptor, the GluR6 receptor, or both receptors, relative to other kainate receptors or AMPA receptors (i.e., other non-NMDA receptors)). As used herein, "tetrahydrofuro[3,2-b]tetrahydropyrans" refer to a class of compounds having the fused ring structure found in dysiherbaine and are meant to include 2-carboxy-2-(2-carboxy-2-amino-eth-1-yl)-tetrahydrofuro[3,2-b]tetrahydropyrans, where the 2-position refers to the non-fused carbon adjacent the oxygen atom in the furan ring. The terms "selective GluR5 receptor antagonist" and "selective GluR6 receptor antagonist" are defined above and are meant to refer to those compounds which selectively bind to GluR5 receptors, or GluR6 receptors, respectively, relative to other kainate receptors (e.g., the GluR7, KA1, and KA2 receptors) or AMPA receptors (e.g., the GluR1, GluR2, GluR3, and GluR4 receptors), which collectively may be referred to as "other non-NMDA receptors."

Examples of compounds have been discussed hereinabove, and all such examples of compounds can be used in the treatment methods disclosed herein. Illustratively, the treatment methods disclosed herein may be practiced using a selective tetrahydrofuro[3,2-b]tetrahydropyran GluR5 receptor antagonist or a selective tetrahydrofuro[3,2-b]tetrahydropyran GluR5 receptor antagonist having Formula I.

The disclosed compounds may be used to prepare pharmaceutical compositions for administering in methods of treating a "neurological disorder or a neurodegenerative disease." As used herein, "neurological disorder or neurodegenerative disease" is meant to include neuropathic pain and other forms of aberrant nociception as well as migraines, and epilepsy, and other neurological disorders. Examples of such neurological disorders or neurodegenerative diseases include Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and post-traumatic pain.

As used herein, the term "migraine" refers a disorder of the nervous system characterized by recurrent attacks of head pain (which are not caused by a structural brain abnormality such as those resulting from tumor or stroke), gastrointestinal disturbances, and possibly neurological symptoms such as visual distortion. Characteristic headaches of migraine usually last one day and are commonly accompanied by nausea, emesis, and photophobia. Migraine can be a "chronic" condition. The term "chronic," as used herein, means a condition of slow progress and long continuance. As such, a chronic condition can be treated when it is diagnosed, and treatment can be continued throughout the course of the disease. Conversely, the term "acute" means an exacerbated event or attack, of short course, followed by a period of remission. Thus, the treatment of migraine contemplates both acute events and chronic conditions. In an acute event, the aforementioned compounds can be administered at the onset of symptoms and discontinued when the symptoms disappear. As described above, a chronic condition can be treated throughout the course of the disease, Suitable subjects include, for example mammals, such as rats, mice, cats, dogs, monkeys, and humans. Suitable human subjects include, for example, those who have previously been determined to be at risk of having or developing Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and/or post-traumatic pain. Other suitable human subjects include, for example, those who have been diagnosed as having Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; posttraumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and/or post-traumatic pain. Still other suitable human subjects include, for example, those who have not been diagnosed as having and/or who have not previously been determined to be at risk of having or developing one or more of the following: Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and post-traumatic pain.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with GluR5 receptor activity and/or GluR6 receptor activity. The disclosed methods may include administering an effective amount of the disclosed compounds (e.g., as present in a pharmaceutical composition) for treating a neurological disorder or neurodegenerative disease.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the neurological disorder or neurodegenerative disease involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

The selective tetrahydrofuro[3,2-b]tetrahydropyran GluR5 receptor antagonists and/or GluR6 receptor antagonists for use according to the methods of disclosed herein may be a single compound or a combination of compounds. For example, the methods disclosed herein may be practiced using a composition containing a single receptor antagonist, or it can be practiced using a composition containing two or more receptor antagonists. The method disclosed herein may be practiced using a composition containing a selective tetrahydrofuro[3,2-b]tetrahydropyran GluR5 receptor antagonist and a selective tetrahydrofuro[3,2-b]tetrahydropyran GluR6 receptor antagonist, which may be the same single compound or two different compounds. The aforementioned compositions may optionally contain one or more other active agents such as those disclosed in U.S. Pat. No. 6,759,418 to Filla et al., which is hereby incorporated by reference, and/or in WO 98/45270, which is hereby incorporated by reference. Additionally or alternatively, the aforementioned compositions can optionally contain one or more non-selective GluR5 receptor antagonists or non-selective GluR6 receptor antagonist (i.e., a compound that is an antagonist of one or more glutamate receptors other than GluR5 and GluR6); or the aforementioned compositions can be substantially free of non-selective GluR5 receptor antagonists and/or non-selective GluR6 receptor antagonists. Still additionally or alternatively, the aforementioned compositions can optionally contain one or more compounds capable of blocking activity at one or more other glutamate receptors (e.g., GluR7 receptors, KA-1 receptors, KA-2 receptors, or other kainate receptors; GluR1 receptors, GluR2 receptors, GluR3 receptors, GluR4 receptors, or other AMPA receptors); or the aforementioned compositions can be substantially free of compounds capable of blocking activity at one or more other glutamate receptors (e.g., GluR7 receptors, KA-1 receptors, KA-2 receptors, or other kainate receptors; GluR1 receptors, GluR2 receptors, GluR3 receptors, GluR4 receptors, or other AMPA receptors).

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

As one skilled in the art will also appreciate, the formulation can be prepared with materials (e.g., actives excipients, carriers, diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight % |
|---|---|
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| | |
|---|---|
| Active Ingredient | 100 mg |
| Mannitol | 100 mg |
| 5 N Sodium hydroxide | 200 ml |
| Purified water to total | 5 ml |

ILLUSTRATIVE EMBODIMENTS

The following embodiments are illustrative and are not intended to limit the disclosed subject matter.

Embodiment 1

A pharmaceutical composition comprising:
(a) an effective amount of a compound having the formula:

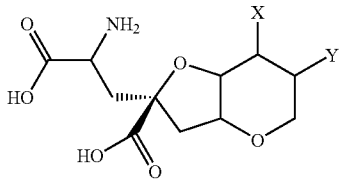

or a salt, ester, amide, or solvate thereof, wherein X and Y may be the same or different and are selected from the group consisting of H, OH, $NH_2$ (optionally substituted with $C_{1-6}$ alkyl such as a substituent NHMe), or halide (e.g., fluoro, chloro, bromo, or iodo); and
(b) one or more pharmaceutically acceptable carriers, diluents, or excipients.

Embodiment 2

The composition of embodiment 1 wherein the compound has the formula:

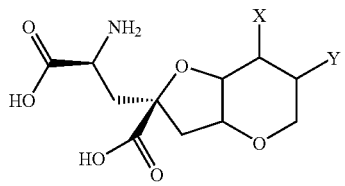

Embodiment 3

The composition of embodiment 1 or 2, wherein X is OH.

Embodiment 4

The composition of any of embodiments 1-3, wherein Y is OH.

Embodiment 5

The composition of any of embodiments 1-4, wherein X and Y are OH.

Embodiment 6

The composition of any of embodiments 1-5, wherein the compound has the formula:

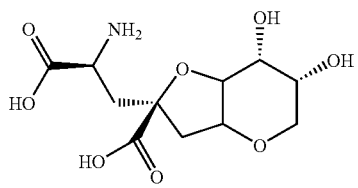

Embodiment 7

The composition of any of embodiments 1 and 3-5, wherein the compound has the formula:

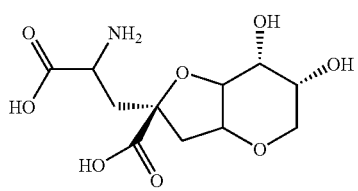

Embodiment 8

The composition of any of embodiments 1-7, wherein the composition is suitable for administration to a human

Embodiment 9

The composition of any of embodiments 1-8, wherein the composition is suitable for oral administration.

Embodiment 10

The composition of any of embodiments 1-8, wherein the composition is suitable for transdermal administration.

Embodiment 11

The composition of any of embodiments 1-8, wherein the composition is suitable for treating a neurological disorder or neurodegenerative diseases selected from the group consisting of Alzheimer's Disease, Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and post-traumatic pain.

Embodiment 12

The composition of any of embodiments 1-11, wherein the composition comprises an effective amount of the compound for selectively antagonizing a GluR5 receptor, a GluR6 receptor, or both receptors.

Embodiment 13

The composition of claim 12, wherein the effective amount is effective for treating a neurological disorder or neurodegenerative diseases selected from the group consisting of Alzheimer's Disease, Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and post-traumatic pain.

Embodiment 14

A method of treating a neurological disorder or a neurodegenerative disease in a subject, the method comprising administering to the subject a pharmaceutical composition of any of embodiments 1-13.

Embodiment 15

A method for selectively antagonizing a GluR5 receptor or a GluR6 receptor, the method comprising contacting the receptor with a compound having the formula:

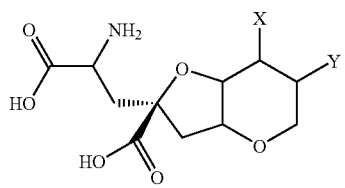

or a salt, ester, amide, or solvate thereof, wherein X and Y may be the same or different and are selected from the group consisting of H, OH, $NH_2$ (optionally substituted with $C_{1-6}$ alkyl such as a substituent NHMe), or halide (e.g., fluoro, chloro, bromo, or iodo); or halide.

Embodiment 16

The method of embodiment 15, wherein the compound has the formula:

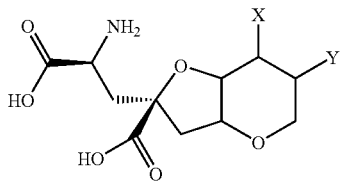

Embodiment 17

The method of embodiment 15 or 16, wherein X is OH.

Embodiment 18

The method of any of embodiments 15-17, wherein Y is OH.

Embodiment 19

The method of any of embodiments 15-18 wherein X and Y are OH.

Embodiment 20

The method of any of embodiments 15-19, wherein the compound has the formula:

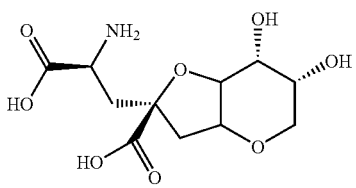

Embodiment 21

The method of any of embodiments 15-20, wherein the contacting is performed in vivo.

Embodiment 22

The method of any of embodiments 15-21, wherein the contacting is performed in vitro.

Embodiment 23

The method of any of embodiments 15-22, wherein the receptor is contacted with an effective concentration of the compound for selectively antagonizing the receptor.

EXAMPLES

The following examples are illustrative and are not intended to limit the disclosed subject matter.

Example 1

Figure 2:
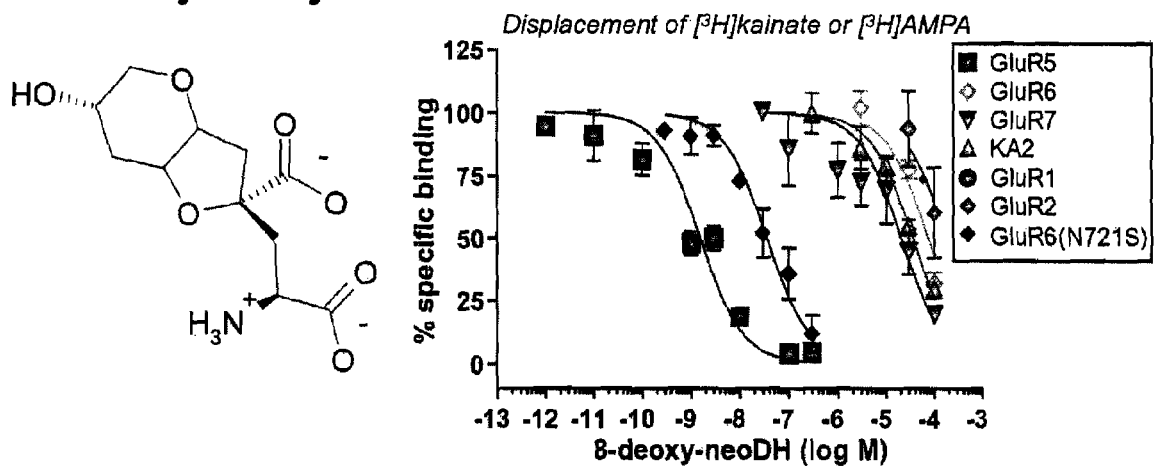
FIG. 2 provides the structure for 8-deoxy-neoDH and 9-deoxy-neoDH and illustrates that deoxy analogs of neoDH retain affinity for GluR5 KAR subunits.
Figure 2:
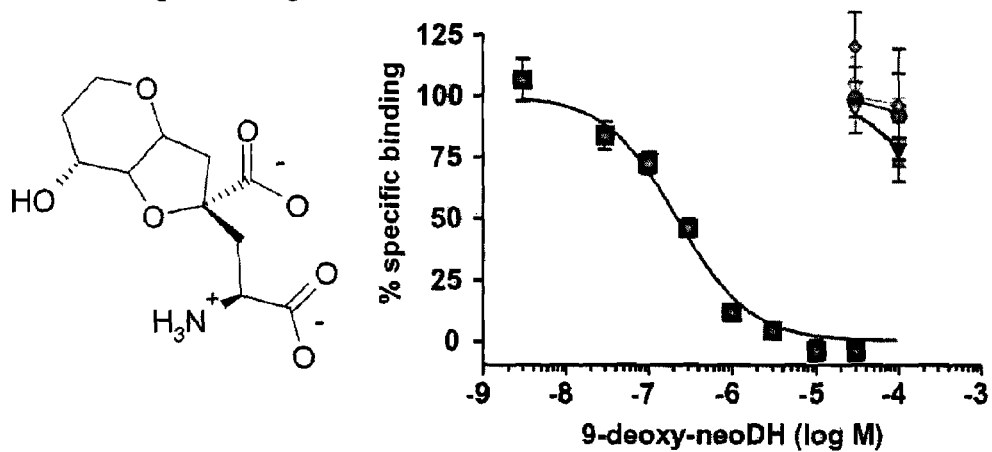

Dysiherbaine (DH) was used as a template for generating novel KAR ligands. (See FIG. 1.) These included 8-deoxy and 9-deoxy analogs of neodysiherbaine (neoDH). (See FIG. 2.) The binding of these analogs to glutamate receptors was assessed by radioligand binding as follows. Membrane preparations from COS-7 or HEK-T/17 cells were isolated 2-3 days after transfection. Displacement assays were performed as described previously (Swanson et al., NEURON 1997; 19:913-26). Unlabeled marine toxin analogs were used to displace [$^3$H]kainate or [$^3$H]AMPA (PerkinElmer) from kainate and AMPA receptors, respectively. (See FIG. 2 and Table 1.)

TABLE 1

|  | GluR5 | GluR6 | GluR7 | KA2 | GluR1 | GluR2 |
|---|---|---|---|---|---|---|
| neodysiherbaine | 7.7 nM | 33 nM |  | 0.6 μM |  |  |
| MSVIII-19 | 128 nM | >100 μM |  | >100 μM | >100 μM | >100 μM |
| 8-deoxy-neoDH | 1.1 nM | 76 μM | 21 μM | 36 μM | >100 μM | >100 μM |
| 9-deoxy-neoDH | 168 nM | >100 μM | >100 μM | >100 μM | >100 μM | >100 μM | n = 3-5 for each concentration of analog

Figure 3:
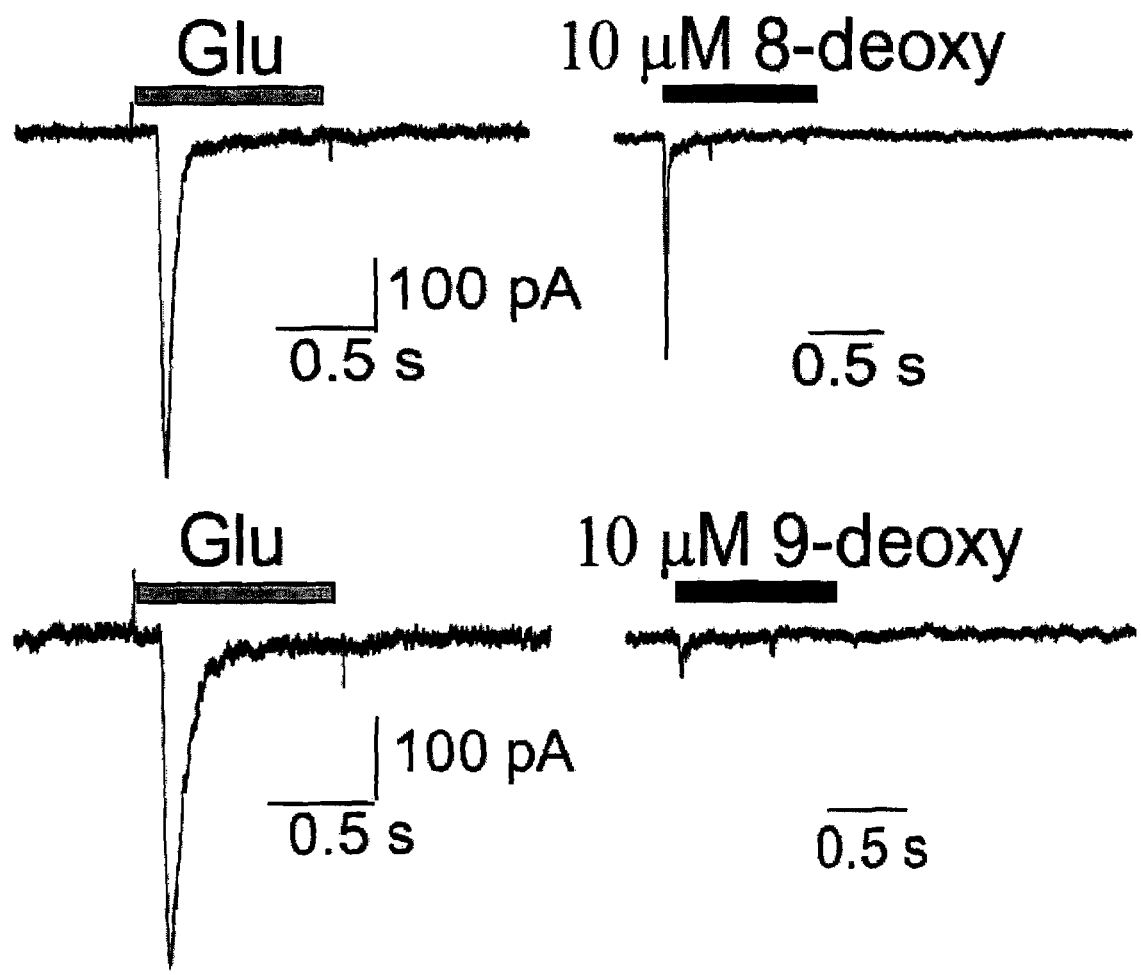
FIG. 3 provides the results of electrophysiology experiments and illustrates that 8-deoxy-neoDH and 9-deoxy-neoDH are GluR5 agonists.

Non-specific binding was defined in the presence of 1 mM glutamate. The effect of these analogs on electrophysiology was assessed as follows. HEK 293 cells were transfected with receptor cDNAs in combination with eGFP cDNA. Patch-clamp recordings from transfected cells were made 24-72 hours later using a fast application system described previously (Swanson et al., NEURON 1997; 19:913-26). (See FIG. 3.)

Figure 4:
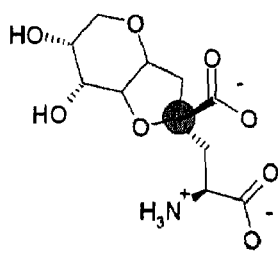
FIG. 4 provides the structures for 4-epi-neoDH; 8-epi-neoDH; 9-epi-neoDH; and 8,9-epi-neoDH and illustrates that epimer analogs of neo DH display altered affinity for KAR subunits.
Figure 4:
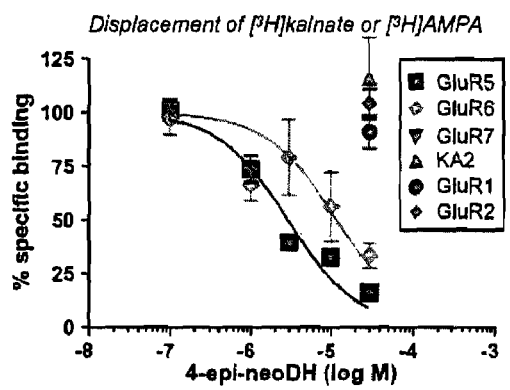
Figure 4:
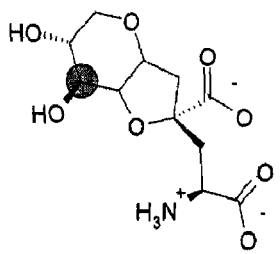
Figure 4:
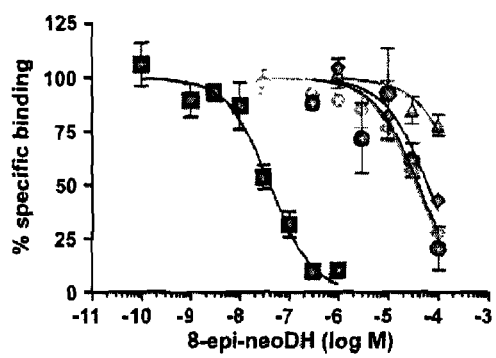
Figure 4:
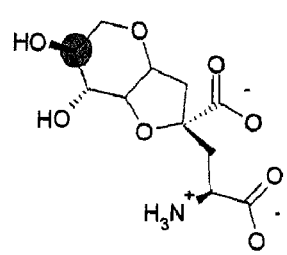
Figure 4:
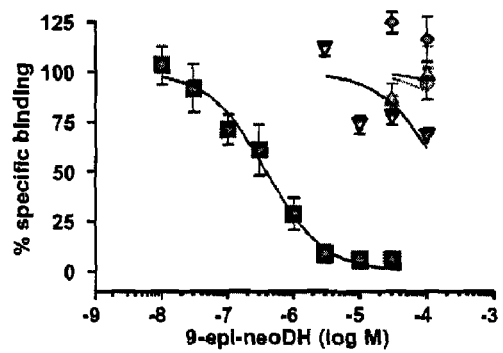
Figure 4:
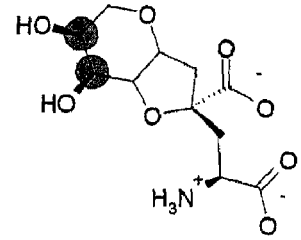
Figure 4:
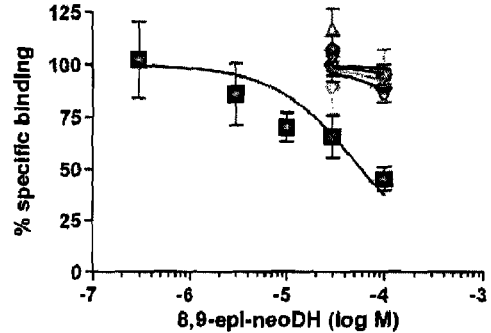

Additional epimer analogs were generated. These included 4-epi-neodysiherbaine, 8-epi-neodysiherbaine, 9-epi-neodysiherbaine, and 8,9-epi-neodysiherbaine. (See FIG. 4.) The binding of these analogs to glutamate receptors was assessed by radioligand binding as described above. (See FIG. 4 and Table 2.)

TABLE 2

|  | GluR5 | GluR6 | GluR7 | KA2 | GluR1 | GluR2 |
|---|---|---|---|---|---|---|
| neodysiherbaine | 7.7 nM | 33 nM |  | 0.6 μM |  |  |
| 4-epi-neoDH | 2.4 μM | 7.7 μM |  | >100 μM | >100 μM | >100 μM |
| 8-epi-neoDH | 34 nM | 22 μM |  | >100 μM | 17 μM | 23 μM |
| 9-epi-neoDH | 296 nM | >100 μM | >100 μM | >100 μM | >100 μM | >100 μM |
| 8,9-epi-neoDH | 48 μM | >100 μM | >100 μM | >100 μM | >100 μM | >100 μM | n = 3-5 for each concentration of analog

Figure 5:
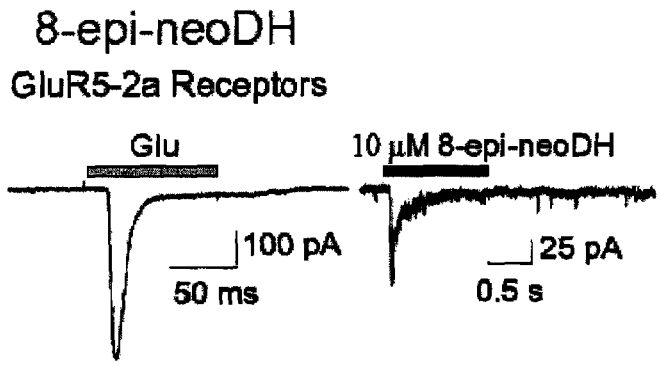
FIG. 5 provides the results of electrophysiology experiments and illustrates that 8-epi-neoDH is a GluR5 agonist; 8,9-epi-neoDH is a GluR5 antagonist; and 4-epi-neoDH is a GluR5/GluR6 antagonist.
Figure 5:
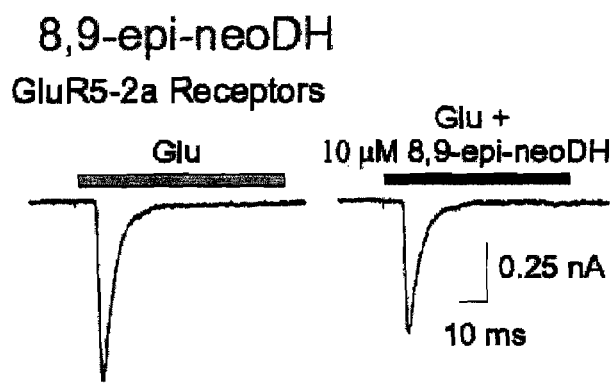
Figure 5:
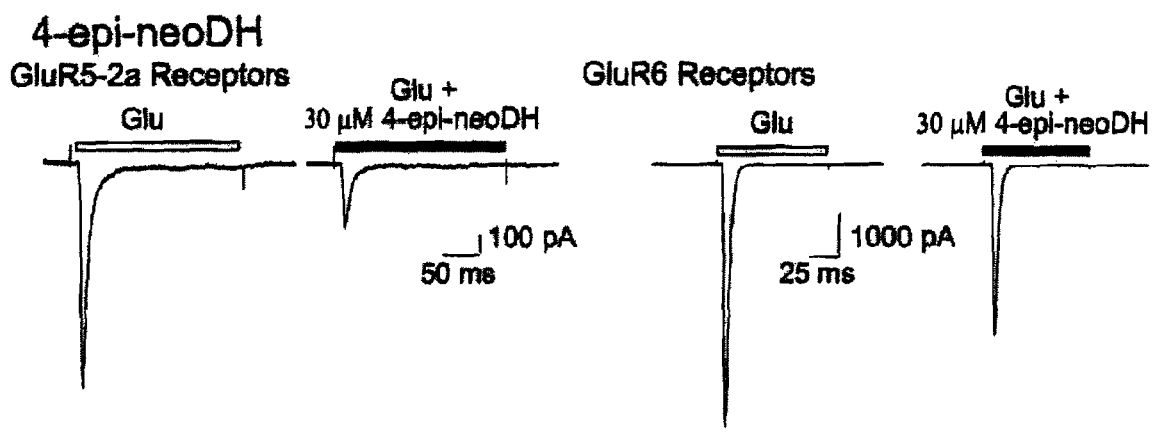
Figure 6:
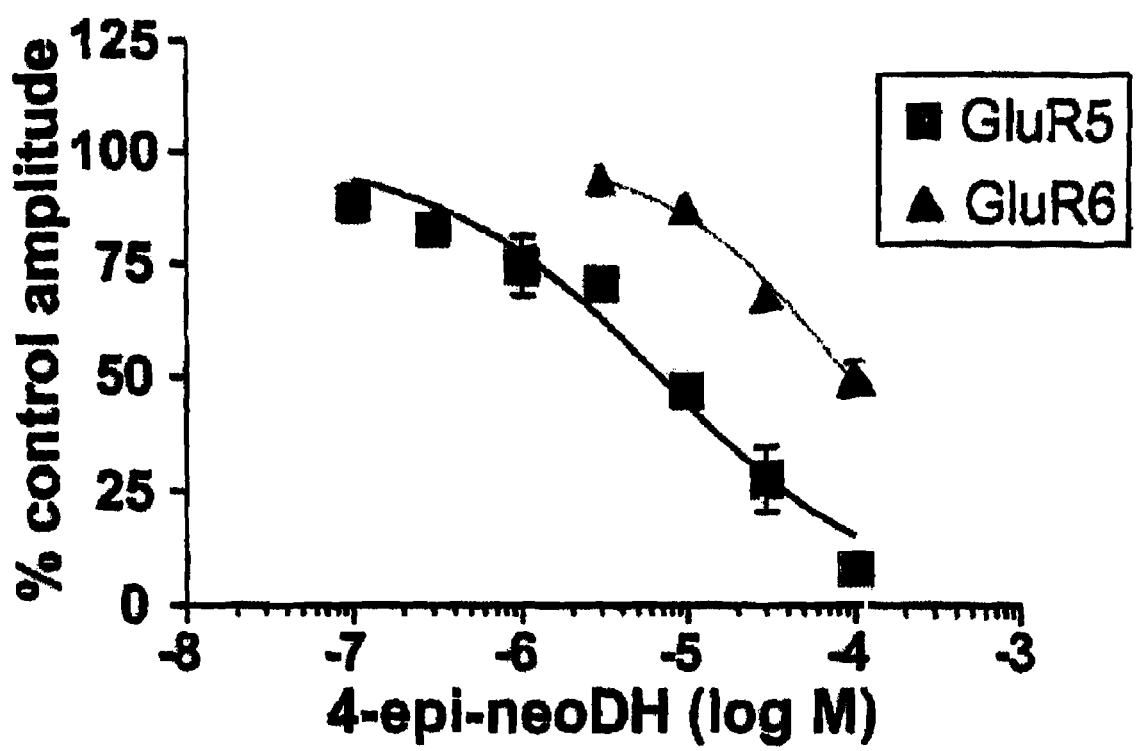
FIG. 6 provides a graph of "% control of amplitude" versus log of the molar concentration of 4-epi-neoDH based on the results provided in FIG. 5 for the electrophysiology experiments. IC50's were estimated for GluR5 (6.9 µM) and for GluR6 (94.5 µM).

The effect of these analogs on electrophysiology also was assessed as described above. (See FIG. 5 and FIG. 6.) The results indicate that the epimer analog 4-epi-neoDH is a GluR5/GluR6 antagonist and the epimer analog 8,9-epi-neoDH is a GluR5 antagonist. In contrast, the epimer analogs 8-deoxy-neoDH, 9-deoxy-neoDH, and 8-epi-neoDH are GluR5 agonists. The results further indicate that the C8 and C9 substituents are necessary for binding to all AMPA and KAR subunits except for GluR5 subunits. The C9 polar group must be present and in the correct spatial orientation for high-affinity GluR5 subunit binding. Inter-domain contacts mediated by residue 721S are critical determinants of binding affinity. The epimer analog 9-deoxy-neoDH mimics the binding affinity of the di-deoxy analog MSVIII-19, but acts as an agonist rather than an antagonist.

Example 2

Reference is made to Lash et al., "Novel Analogs and Stereoisomers of the Marine Toxin Neodysiherbaine with Specificity for Kainate Receptors," JPET 2008; 324: 484-496, the content of which is incorporated herein by reference.

Abstract

Antagonists for kainate receptors (KARs), a family of glutamate-gated ion channels, are efficacious in a number of animal models of neuropathologies, including epilepsy, migraine pain, and anxiety. In order to produce molecules with novel selectivities for kainate receptors, we generated three sets of analogs related to the natural marine convulsant neodysiherbaine (neoDH) and characterized their pharmacological profiles. Radioligand displacement assays with recombinant AMPA and KARs demonstrated that functional groups at two positions on the neoDH molecule are critical pharmacological determinants; only binding to the GluR5-2a subunit was relatively insensitive to structural modifications of the critical functional groups. NeoDH analogs in which the L-glutamate congener was disrupted by epimerization retained low affinity for GluR5-2a and GluR6a KAR subunits. Most of the analogs showed agonist activity in electrophysiological recordings from HEK-T/17 cells expressing GluR5-2a KARs, similar to the natural convulsant neoDH. In contrast, 2,4-epi-neoDH inhibited glutamate currents evoked from both GluR5-2a and GluR6a receptor-expressing cells. This compound therefore represents the first compound to exhibit functional antagonist activity on GluR5-2a and GluR6a KAR subunits without concurrent activity on AMPAR subunits. Finally, binding affinity of the synthetic ligands for the GluR5-2a subunit closely correlated with their seizurogenic potency, strongly supporting a role for receptors containing this subunit in the convulsant reaction to KAR agonists. The analogs described here offer further insight into structural determinants of ligand selectivity for KARs and potentially represent useful pharmacological tools for studying the role of KARs in synaptic physiology and pathology.

Introduction

Kainate receptors (KARs) are a family of ionotropic glutamate receptors that play a variety of roles in the mammalian brain. They contribute to excitatory postsynaptic transmission at some synapses, modulate excitatory and inhibitory neurotransmission from presynaptic loci, and modify network excitability through actions on neuronal ion channels (reviewed by Lerma, 2006; Pinheiro and Mulle, 2006). Targeting KARs could be a useful strategy for therapy in a number of neurological diseases because antagonists are efficacious in animal models of epilepsy (Smolders et al., 2002), neuropathic and migraine pain (Filla et al., 2002; Weiss et al., 2006), and anxiety (Alt et al., 2007).

Successful manipulation of neuronal KARs, which are selectively targeted and comprised of distinct subunit stoichiometries, will require expansion of the existing set of pharmacological agents. KAR subunits assemble to form tetrameric channels composed of the obligate GluR5, GluR6, or GluR7 subunits alone or in heteromeric combination with KA1 and KA2 subunits, which do not form functional homomeric receptors (Werner et al., 1991; Herb et al., 1992; Hollmann and Heinemann, 1994). At present, the majority of KAR antagonists and agonists with any degree of selectivity target receptors containing the GluR5 subunit. Furthermore, no compounds exist that broadly inhibit KARs (of all stoichiometries) without also antagonizing AMPARs (Kew and Kemp, 2005). For example, substitution at the 5-position of the uracil ring of N3 substituted willardiine derivatives generates potent and selective GluR5 KAR antagonists (Dolman et al., 2007). Noncompetitive antagonists also exist for GluR5-containing receptors (Valgeirsson et al., 2003; Christensen et al., 2004; Valgeirsson et al., 2004). A GluR6 antagonist has been described, but this compound, NS-102, has seen only limited use because of insolubility and questions regarding its subunit selectivity (Patemain et al., 1996; Lerma et al., 2001). Thus, there remains a compelling need for the development of ligands with a larger spectrum of specificity for KAR subunits and general KAR antagonists without activity at AMPARs.

Towards that end, we have been interested in natural source compounds as tools to probe KAR function at both the structural level and in neurotransmission. We previously showed that dysiherbaine (DH), a marine toxin from the sponge *Dysidea herbacea*, is a high-affinity, subunit-selective KAR agonist and consequently a potent convulsant (Sakai et al., 1997; Sakai et al., 2001b). Structurally, DH shares a glutamate congener with other KAR agonists such as kainate and domoate, but is distinct in that it contains a tetra-substituted hydrofuropyran ring system with two functional groups, at the C8 and C9 positions, that largely control selectivity for AMPA and kainate receptors (Sasaki et al., 1999; Sakai et al., 2001a). Further characterization of a natural analog of DH, neodysiherbaine (neoDH), and a C8/C9 di-deoxy synthetic analog of DH, MSVIII-19, revealed that slight structural modifications cause significant changes in the pharmacological activity, including generation of a functional antagonist for GluR5 containing receptors in MSVIII-19 (Sasaki et al., 1999; Sakai et al., 2001a; Sanders et al., 2005).

In order to determine how additional modification of the template structure could alter activity on KARs, new analogs of neoDH were synthesized and characterized using radioligand binding assays and patch-clamp analysis in this study. First, the C8 and C9 hydroxyl groups were removed individually (deoxy analogs) to generate the intermediate analogs between neoDH and MSVIII-19. In a second set of analogs, the stereochemistry of the C8 and C9 hydroxyl groups was reversed both individually and concurrently. Finally, a third set of analogs with altered chirality of the C2 and C4 carbons were tested for activity; these compounds were generated as bi-products of the total synthesis of neoDH previously and were significantly less seizurogenic than the parent neoDH compound (Shoji et al., 2006). To elucidate analog binding and specificity at the atomic level, we carried out molecular dynamic simulations for the ligand-binding domain of the GluR5 KAR subunit with docked ligands. Our data demonstrates that the spatial orientation of the C8 and C9 functional groups in the neoDH molecule also are critical determinants of pharmacological activity and that structural modification within the glutamate congener offers potential for the generation of compounds with novel pharmacological profiles on KARs. We also found a high degree of correlation between the binding affinity for the GluR5-2a subunit and seizurogenic potency of the analogs, supporting a central role for receptors containing this subunit in induction of convulsions.

Materials and Methods

Cell Culture and Electrophysiology. HEK-293-T/17 cells were maintained in Dulbecco's modified Eagle's medium (DMEM) supplemented with 100 μg/mL penicillin, 100 μg/mL streptomycin, and 10% heat inactivated fetal bovine serum. One day before transfection, HEK-T/17 cells were plated at low density on glass coverslips coated with 100 μg/ml poly-D-lysine and 100 μg/ml collagen. Cells were transfected with receptor cDNAs (0.05-0.2 pg) in combination with enhanced green fluorescent protein (eGFP) cDNA for visualization of transfected cells. Transfections were carried out with Fugene6 (Roche Applied Science) according to the manufacturer's protocol and used 2-3 days following transfection. Internal solution consisted of 110 mM CsF, 30 mM CsCl, 4 mM NaCl, 0.5 mM CaCl2, 10 mM HEPES, and 5 mM EGTA, and was adjusted to pH=7.3 with CsOH. The external solution contained 150 mM NaCl, 2.8 mM KCl, 2 mM CaCl2, 1 mM MgCl2, and 10 mM HEPES, adjusted to pH=7.3 with NaOH. Patch electrodes from thick-walled borosilicate glass (Warner Instruments, Hamden, Conn.) were pulled to a final resistance of 1.5 to 2.5 MO after fire polishing. Drugs were applied with fast application through a three barrel glass tube mounted on a piezo-bimorph; glutamate-evoked currents from transfected cells lifted into the laminar solution flow had a 10-90% rise-time of 0.8-1.5 ms (Swanson et al., 1997). Several drug reservoirs fed into each glass barrel through manifolds, and these had an effective exchange rate between drug solutions of ~1 min. To determine the pre-desensitization IC50 of selected analogs, several control glutamate (10 mM) applications were followed by a 2.5 minute application of various concentrations of 8-deoxy-neoDH, 9-deoxy-neoDH, or MSVIII-19, after which the analogs were co-applied with glutamate. A similar protocol was followed to measure the recovery of glutamate-evoked currents, with the exception that the analogs were not co-applied with glutamate. Whole cell patch clamp recordings were carried out using an Axopatch 200B amplifier (Axon Instruments). Data were analyzed with Origin 7.5 (OriginLab Corp.), and Prism4 (GraphPad Software Inc.); inhibition-response curves were plotted and fit with a one-site competition curve constrained to fixed minima (0) and maxima (100).

Materials. Analogs of neoDH were synthesized as described (Shoji et al., 2006) and dissolved in ddH2O.

Radioligand binding. Membrane preparations from HEK-293-T/17 cells were prepared and used in radioligand binding assays as described previously (Sanders et al., 2005). Unlabeled analogs were used to displace [3H]kainate (10-20 nM, PerkinElmer Life and Analytical Sciences, Boston, Mass.) or [3H]AMPA (20 nM, PerkinElmer Life and Analytical Sciences, Boston, Mass.) from KARs and AMPARs, respectively. Nonspecific binding was determined in the presence of 1 mM glutamate. After 1 hour incubation at 4° C., samples were harvested by rapid filtration onto Whatman GF/C membranes. Upon addition of scintillation fluid, membranes were incubated for 1 hour at room temperature. A Beckman LS5000TD scintillation counter was used for quantification (Beckman Coulter Inc., Fullerton, Calif.). Data were plotted and fit with a one-site competition curve with fixed minima and maxima using Prism 4 (GraphPad Software, Inc). Ki's were calculated with the Cheng-Prusoff equation using the determined IC5o values and the radioligand Kd. Data were plotted and fit with a one-site competition curve with fixed minima (0) and maxima (100) (Prism4, GraphPad Software, Inc.). Correlation analysis was performed with these binding data and the seizure activity of each analog, represented as ED50 values.

Results

Figure 7:
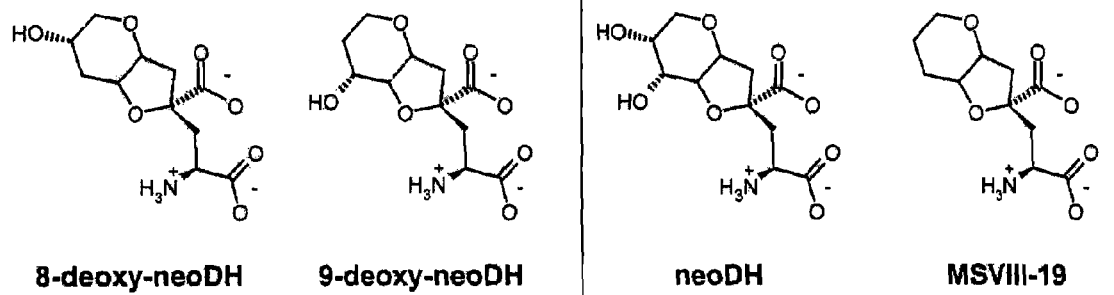
FIG. 7 provides the chemical structures of the three groups of synthetic neodysiherbaine-derived analogs. The parent marine toxin, neodysiherbaine (neoDH), and the first synthetic analog, MSVIII-19, are outlined in a box in the first row of structures. The analog "neoDH" contains a glutamate backbone connected to a rigid ring structure with hydroxyl groups at both the C8 and C9 ring positions; MSVIII-19 is the di-deoxy synthetic analog. Group 1 analogs are the deoxy analogs at the C8 and C9 ring positions. Group 2 analogs are epimer analogs that manipulate the orientation of the substituents at the C8 and C9 ring positions. Group 3 analogs are epimer analogs at the C2/C4 positions within the glutamate backbone of the parent compound. The carbon configurations changed are indicated by shaded gray circles.
Figure 7:
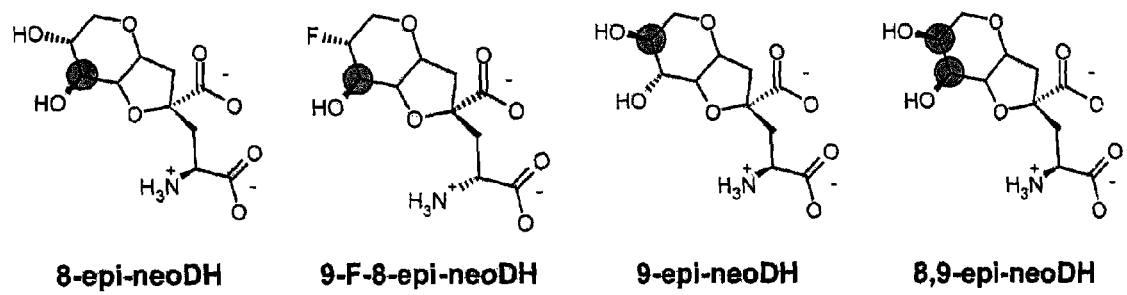
Figure 7:
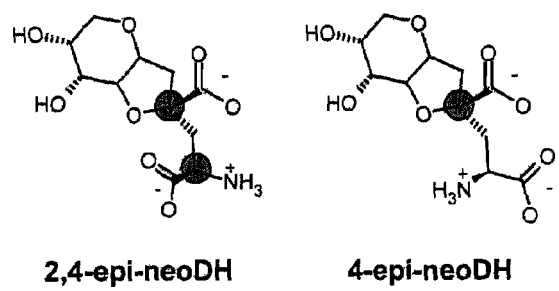

In order to characterize the molecular determinants of selectivity and specificity of KAR ligands that are structurally related to the marine convulsant neoDH, we synthesized representatives of three types of analogs (FIG. 7). Group 1 analogs lack the hydroxyl group additions at the C8 and C9 ring positions that were previously identified as important determinants of pharmacological activity and selectivity (Sanders et al., 2006); they therefore represent intermediates between the natural di-hydroxyl high-affinity agonist neoDH and the di-deoxy synthetic analog, MSVIII-19, which acts as a selective GluR5 antagonist (Sanders et al., 2005). The other groups consist of stereoisomeric analogs designed to test the importance of the spatial orientation of the C8 and C9 hydroxyl moieties (Group 2) and the C2 and C4 carbons within the L-glutamate congener of the parent molecule (Group 3) (Shoji et al., 2006).

Deoxy Analogs Retain Affinity and Agonist Activity on GluR5 KAR Subunits

Figure 8:
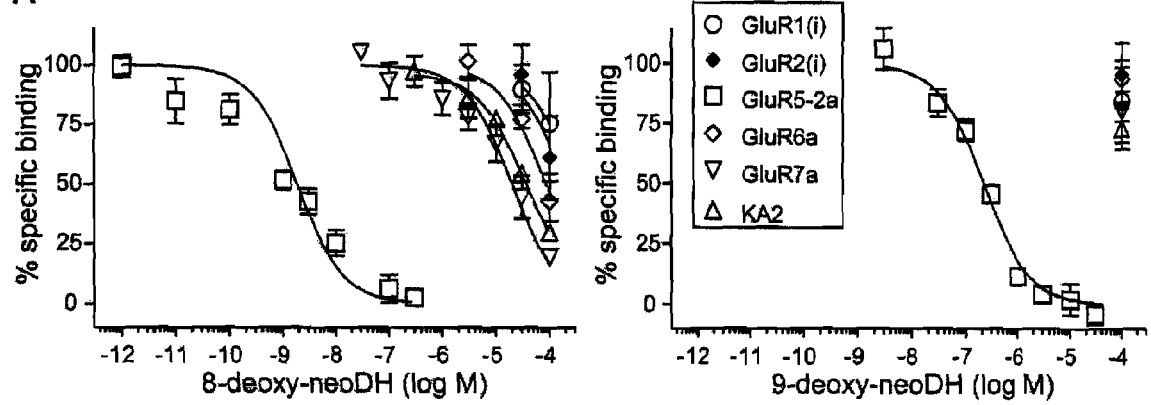
FIG. 8 illustrates that deoxy analogs retain high affinity only for GluR5 subunits: A, Displacement of [3H]kainate and [3H]AMPA from KA and AMPARs, respectively for 8-deoxy-neoDH (left), 9-deoxy-neoDH (right). 1 mM glutamate was used to determine nonspecific binding. Curves were fit with a one-site competition curve with fixed minima (0%) and maxima (100%). n=3-5 for each concentration of analog on each receptor subunit. Ki's were calculated with the Cheng-Prusoff equation using the determined IC50 values and the radioligand Kd and are in Table 3; B, Both deoxy analogs are GluR5 agonists. Traces are representative of single control responses after 100 ms application of saturating concentrations of glutamate (10 mM) to GluR5-2a-expressing cells and analog-evoked currents during a 1 s application for 100 µM 8-deoxy-neoDH (left) and 100 µM 9-deoxy-neoDH (right).
Figure 8:
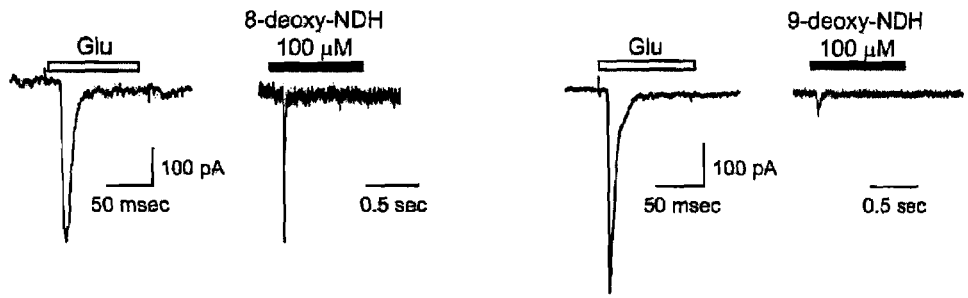

The pharmacological profiles of the Group I analogs, 8-deoxy-neoDH and 9-deoxyneoDH, were analyzed initially in radioligand binding experiments with expressed recombinant AMPA and kainate receptor subunits. Displacement of [3H]kainate from cell membranes with a range of analog concentrations yielded IC50 values that were then used to calculate Ki values for each analog/receptor combination. Both Group 1 analogs retained high affinity only for GluR5-2a KAR subunits (FIG. 8A). The binding affinity of 8-deoxy-neoDH for GluR5-2a subunits (Ki=1.5 nM, n=3-5) was higher than that of the parent compound neoDH (Ki=7.7 nM, Sanders et al., 2005). Because the subunit isoform of GluR5 that is predominantly expressed in the brain is GluR5-2b, we repeated radioligand binding assays with 8-deoxy-neoDH on GluR5-2b subunits and found no substantial change in affinity (Ki=2.0 nM, n=3-5, versus 1.5 nM for GluR5-2a subunits). Weak binding to other KAR and AMPAR subunits was observed, with all Ki values estimated at >10 μM (n=3-5; Table 3, FIG. 8A).

TABLE 3

Ki values of epimer and deoxy analogs

|  | GluR5-2a | GluR6a | GluR7a | KA2 | GluR1(i) | GluR2(i) |
|---|---|---|---|---|---|---|
| neodysiherbaine | 7.7 | 33 |  | 0.6 |  |  |
| MSVIII-19 | 128 | >100 |  | >100 | >100 | >100 |
| 8-deoxy-neoDH | 1.5 | 48 | 2.9 | 20 | >100 | >100 |
| 9-deoxy-neoDH | 169 | >100 | >100 | >100 | >100 | >100 |
| 8-epi-neoDH | 34 | 22 | 1.7 | >100 | 16 | 23 |

TABLE 3-continued

Ki values of epimer and deoxy analogs

|  | GluR5-2a | GluR6a | GluR7a | KA2 | GluR1(i) | GluR2(i) |
|---|---|---|---|---|---|---|
| 9-F-8-epi-neoDH | 28 | >100 | >100 | >100 | >100 | >100 |
| 9-epi-neoDH | 292 | >100 | >100 | >100 | >100 | >100 |
| 8,9-epi-neoDH | 48 | >100 | >100 | >100 | >100 | >100 |
| 2,4-epi-neoDH | 2.4 | 7.7 | >100 | >100 | >100 | >100 |
| 4-epi-neoDH | 559 | 6.7 | >100 | ~30 | >30 | >30 |

Ki values calculated from the displacement curves for each analog on each receptor subunit are shown in Table 3. In Table 3, Ki values for displacement of [$^3$H]kainate and [$^3$H]AMPA by epimer and deoxy analogs of DH on KA and AMPAR subunits were calculated using appropriate Kd values in the Cheng-Prusoff equation (Ki=IC50/(1+[radioligand]/Kd). IC50 values were obtained using a one-site competition fit, with fixed minima (0%) and maxima (100%) using Prism 4 software. Nanomolar concentrations are in bold italics, all other concentrations are micromolar. Ki values are similar to those reported earlier for some of the compounds (Shoji et al., 2006), with the exception of 8-deoxy-neoDH, which was incorrectly reported to have a Ki value of 42 nM in the previous report. For comparison, the Ki values for neoDH and MSVIII-19 are included in the table (Sanders et al., 2005). Removal of the C9 hydroxyl eliminated binding to all receptor subunits (Ki values estimated at >100 µM), with the exception of GluR5-2a KARs. 9-deoxy-neoDH displaced radioligand from these receptors with a Ki of 169 nM (n=3-4, FIG. 8A), which is quite similar to that observed with MSVIII-19, the di-deoxy analog that acts as an antagonist. These data suggest that loss of the substituent at the C9 position largely underlies the difference in binding affinity between neoDH and MSVIII19.

Because neoDH and its natural analog, dysiherbaine (DH), both act as KAR agonists, we tested each of the analogs for agonist activity using whole-cell patch clamp recordings. Application of saturating concentrations of glutamate (10 mM) to a transiently transfected HEK-293-T/17 cell was first done to obtain a rapidly activating and desensitizing control current; this was then followed by a test application of the analog at a high concentration (10-100 µM). Both 8-deoxy-neoDH (100 µM) and 9-deoxy-neoDH (100 µM) elicited currents from GluR5-2a receptors (n=3-4, FIG. 8B), confirming that these compounds are KAR agonists. 8-deoxy-neoDH is likely a full agonist, or a highly efficacious partial agonist, because the amplitude of currents elicited from GluR5 receptors at a concentration of 100 µM were similar to those evoked by saturating concentrations of glutamate. In contrast, 9-deoxy-neoDH was a very weak agonist that evoked only small currents at high concentrations.

Figure 9:
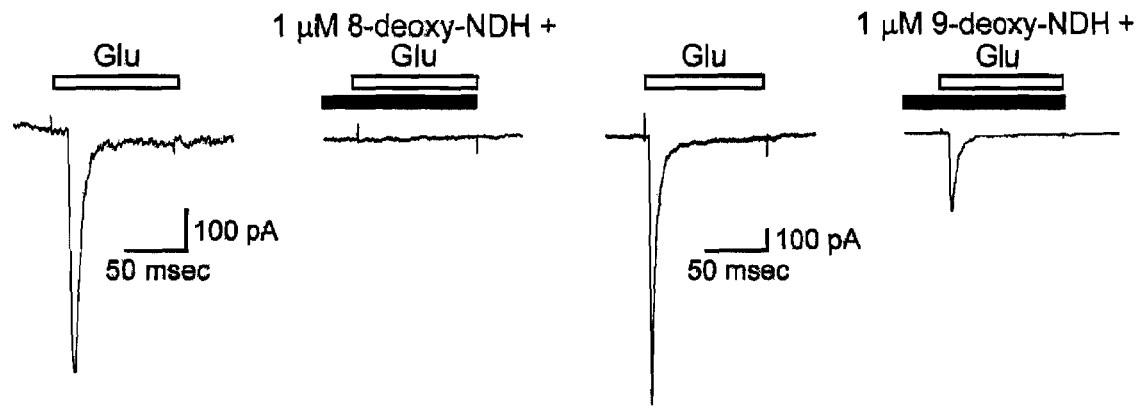
FIG. 9 illustrates that the deoxy analogs and MSVIII-19 differ in potency for pre-desensitization of GluR5-2a receptors: A, Representative traces of glutamate-evoked currents (10 mM) before application of 1 µM 8-deoxy-neoDH (left) or 1 µM 9-deoxy-neoDH; subsequent glutamate-evoked currents in the presence of the analogs were attenuated by desensitization (right); B, Inhibition-response curves for 8-deoxy-neoDH, 9-deoxyneoDH and MSVIII-19 (from Sanders et al., 2005) on recombinant GluR5-2a receptors. Logistic fits were constrained at the minima (0%) and maxima (100%) and IC50 values were determined to be 238 pM for 8-deoxy-neoDH and 151 nM and 23 nM for 9-deoxyneoDH and MSVIII-19, respectively (Sanders et al., 2005), respectively. n=3-5 for each concentration.
Figure 9:
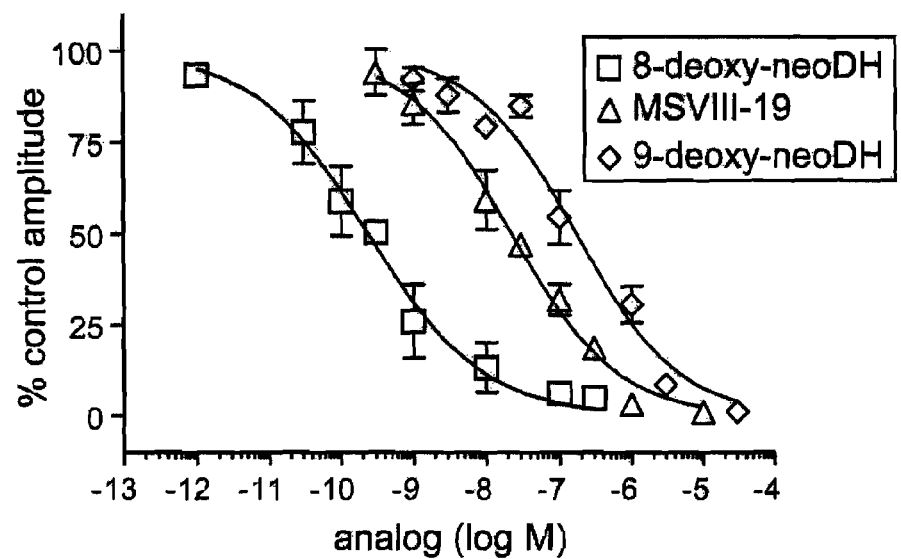

9-deoxy-neoDH and the di-deoxy antagonist, MSVIII-19, have very similar binding profiles on GluR5-2a and other subunits (Sanders et al., 2005), but both their functional activities and behavioral properties differ. 9-deoxy-neoDH elicits small but reproducible currents from GluR5-2a receptors (FIG. 8B), whereas MSVIII-19 behaves as an antagonist (Sanders et al., 2005). To further compare the activity of these compounds and the high-affinity agonist 8-deoxy-neoDH on GluR5-2a receptors, we determined their respective IC50s for pre-desensitization of the receptor (FIG. 9). Responses to 10 mM glutamate were elicited to determine the control current amplitudes for GluR5-2a expressing cells; receptors were then pre-desensitized with low concentrations of the analog (8-deoxy-neoDH or 9-deoxy-neoDH) before test co-applications with glutamate. FIG. 9A shows representative control and test traces in which pre-application of 1 µM 8-deoxy-neoDH completely inhibited a glutamate-evoked current from a GluR5-2a expressing cell. In contrast, 1 µM 9-deoxy-neoDH inhibited but did not abolish glutamate-evoked currents. Pre-desensitization of GluR5-2a receptors occurred in a concentration-dependent manner, as shown in FIG. 9B, which also contains our previous data from similar experiments with MSVIII-19 for comparative purposes (Sanders et al., 2005). Inhibition-response analysis yielded an IC50 value of 151 nM for 9-deoxy-neoDH inhibition of GluR5-2a receptor activation (n=3, FIG. 3B). This is a similar but somewhat less potent inhibitory activity than MSVIII-19, which has an IC50 on GluR5-2a receptors of 23 nM (Sanders et al., 2005). 8-deoxy-neoDH inhibited GluR52a receptor activation more potently with an IC50 value of 238 pM (n=3-4).

Figure 10:
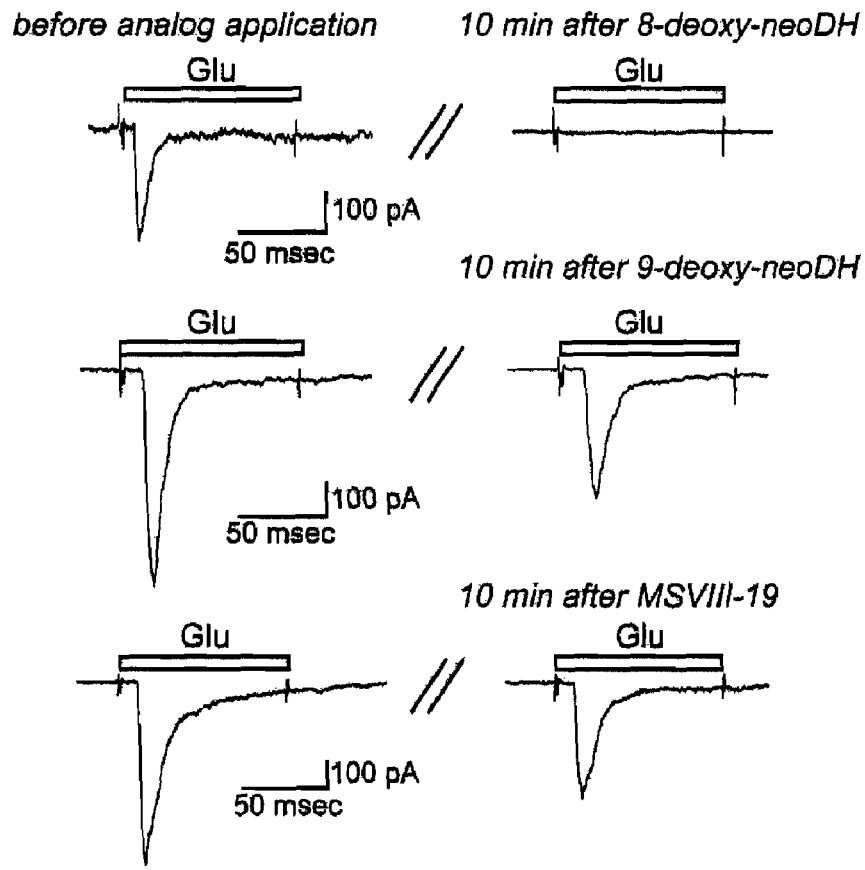
FIG. 10 illustrates recovery of glutamate-evoked currents after analog application is relatively rapid for 9-deoxy-neoDH and MSVIII-19: A, Representative traces of control glutamate evoked currents (left) before ~2.5 min application of 30 µM 8-deoxy-neoDH, 9-deoxyneoDH, or MSVIII-19. Traces on the right are representative of glutamate-evoked currents 10 min after analog application; B, The time course of recovery after application of 30 µM 8-deoxy-neoDH, 9-deoxy-neoDH, or MSVIII-19 on GluR5-2a expressing cells. The graph shows relative peak amplitudes of glutamate-evoked currents (normalized to amplitudes during the 2 min control period) before and following application of the analogs (n=3-6 at each time point). GluR5-2a receptors recovered from desensitization induced by 9-deoxy-neoDH and MSVIII-19 within 3 mins, whereas 8-deoxy-neoDH remained associated beyond the duration of the experiments.
Figure 10:
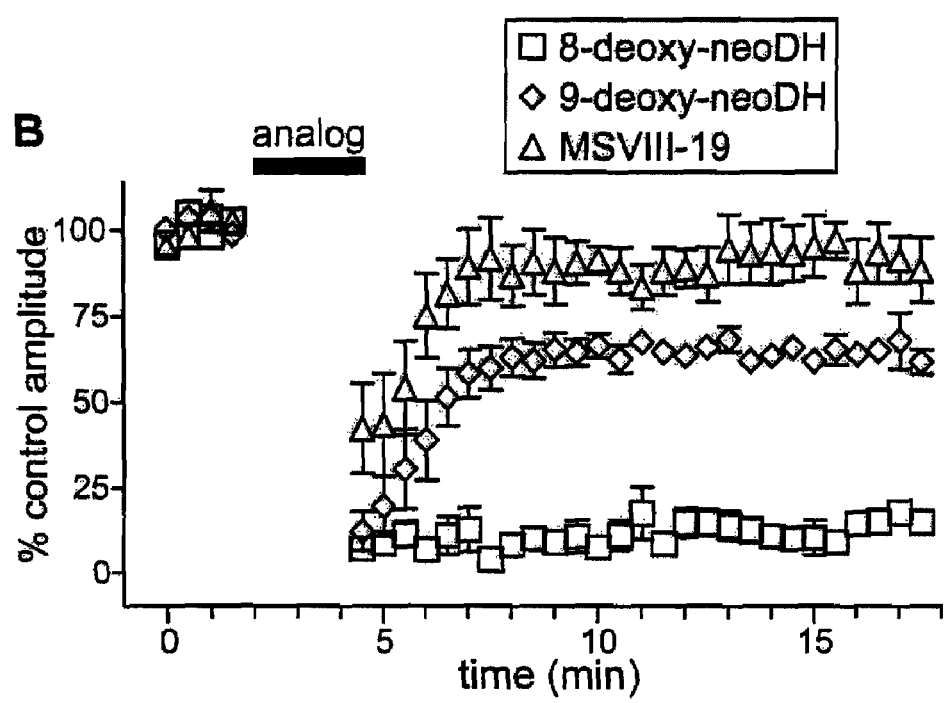

Several analogs, including the parent compounds DH and neoDH, induce a very stable, ligand-bound desensitized conformation of GluR5-2a and GluR6a receptors that occludes subsequent activation of the receptors for long periods of time. We measured the duration of the interaction of Group I analogs with GluR5-2a receptors by determining the time course of recovery of glutamate-evoked currents after application of the analogs (for 2.5 min) (FIG. 10). In FIG. 10A, traces on the left are representative control glutamate-evoked currents; traces on the right are glutamate-evoked currents ten minutes after exposure to 8-deoxy-neoDH, 9-deoxy-neoDH, or MSVIII-19 (each at 30 µM). The high-affinity agonist 8-deoxy-neoDH completely attenuated glutamate currents in response to glutamate for up to 15 min (n=3, FIG. 10B), similar to both DH and neoDH (Swanson et al., 1997; Sanders et al., 2005). In contrast, glutamate elicited large-amplitude currents relatively rapidly after application of either 9-deoxy-neoDH (time constant for recovery, τ=1.5 s, n=3-5) or MSVIII-19 (τ=1.4 s, n=3-6); in both cases the currents returned to an equilibrium amplitudes in −3 minutes. It should be noted that GluR5-2a receptors exhibit significant run-down in current amplitudes under normal conditions, without analog application, to 75-80% of control within 10 min of initiation of whole-cell recording (n=9, see FIG. 14). It is not clear if the degree of attenuation of glutamate currents following 9-deoxy-neoDH, which seems somewhat lower than is accountable for simply by run-down of currents, represents stable binding with a subset of subunits within the tetrameric GluR5-2a receptor, or if it reflects variability in the degree of run-down during those particular recordings. Regardless, these data demonstrate that 9-deoxy-neoDH and MSVIII-19 fail to induce the long-lasting, ligand-bound desensitized state of GluR5-2a receptors observed with DH, neoDH, and 8-deoxy-neoDH (Swanson et al., 1997; Sanders et al., 2005).

C8 and C9 Epimers have Reduced Affinity for KAR Subunits

Figure 11:
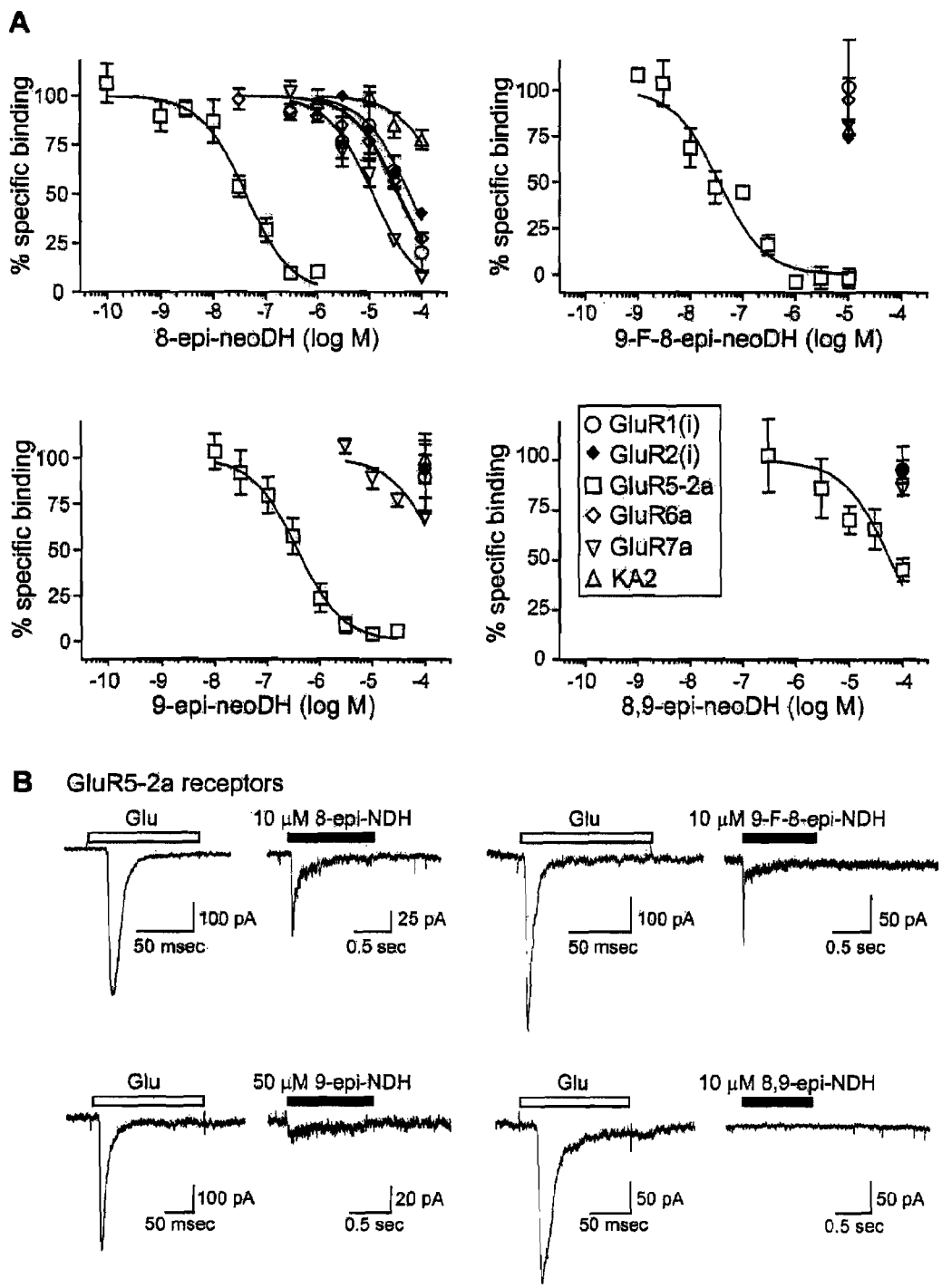
FIG. 11 illustrates that C8 and C9 epimers have reduced affinity for KAR subunits and are agonists: A. Displacement of [3H]kainate and [3H]AMPA from KA and AMPARs, respectively for 8epi-neoDH, 9-F-8-epi-neoDH, 9-epi-neoDH, and 8,9-epi-neoDH. 1 mM glutamate was used to determine nonspecific binding. Curves were fit with a one-site competition curve with fixed minima (0%) and maxima (100%). n=2-5 for each concentration of analog on each receptor subunit. Ki's were calculated with the Cheng-Prusoff equation using the determined IC50 values and the radioligand Kd and are in Table 3; B, Single C8/C9 epimer analogs activate GluR5-expressing cells. Traces represent glutamate-evoked currents (10 mM) from GluR5-2a-expressing cells and analog-evoked currents during a 1 s application of 10 µM 8-epi-neoDH, 10 µM 9-F-8-epi-neoDH, 50 µM 9-epi-neoDH. 10 µM 8,9-epi-neoDH failed to activate GluR5-2a-expressing cells.

To test the importance of the spatial orientation of the critical C8 and C9 substituents in conferring selectivity for KARs, we first determined the affinities of the C8 and C9 epimers on KAR and AMPAR subunits in radioligand binding assays (Table 3, FIG. 11). The single C8 epimer, 8-epi-neoDH, weakly displaced radiolabeled ligand from a number of KAR and AMPAR subunits (Table 3), but had the highest affinity for GluR52a subunits (Ki=34 nM, n=3-5) (FIG. 11A, top left). 9-F-8-epi-neoDH, in which the C9 hydroxyl group was replaced with an electrophilic fluorine, also displaced [3H]kainate selectively from GluR5-2a KAR subunits (Ki=28 nM, n=2-4). In single-point assays (at 10 μM) with other receptor subunits, displacement of radioligand with 9-F-8-epi-neoDH proved very similar to that of 8-epi-neoDH (FIG. 11A, top right). The C9 epimer, 9-epineoDH, displaced [3H]kainate from GluR5-2a subunits (Ki=292 nM, n=3-4), with an affinity-300-fold lower than neoDH, and was inactive at other subunits (FIG. 11A, bottom left). Alteration of the spatial orientation of both the C8 and C9 groups in 8,9-epineoDH effectively eliminated affinity for all receptor subunits, including GluR5-2a (n=34) (Table 3, FIG. 11A, bottom right). These data indicate that GluR5-2a is the only subunit that tolerates alteration of the spatial orientation of the C8 and C9 functional groups. As with the Group 1 deoxy compounds, variation at C8 had less consequence on binding affinity for GluR5-2a compared to the critical C9 group.

In whole-cell patch clamp recordings, 8-epi-neoDH, 9-F-8-epi-neoDH, and 9-epi-neoDH all elicited rapidly activating currents from GluR5-2a-expressing cells (FIG. 11B). 8-epi-neoDH and 9-F-8-epi-neoDH (n=4, 10 μM) elicited large desensitizing currents with variable kinetics; on the other hand, 9-epi-neoDH (n=3, 50 μM) elicited very small amplitude, weakly desensitizing currents relative to the glutamate-evoked controls. 8,9epi-neoDH failed to elicit a detectable current when applied to GluR5-2a-expressing cells at high test concentrations, but modestly inhibited glutamate-evoked currents in GluR5-2a-expressing cells (data not shown); however, 8,9-epi-neoDH has a very low affinity for GluR5-2a KARs and thus any agonist activity may be very weak. Thus, the pharmacological activities and receptor selectivity of these epimeric compounds were generally similar to those of their deoxy counterparts.

C2 and C4 Epimers Maintain Affinity for a Subset of Non-NMDA Receptor Subunits

Figure 12:
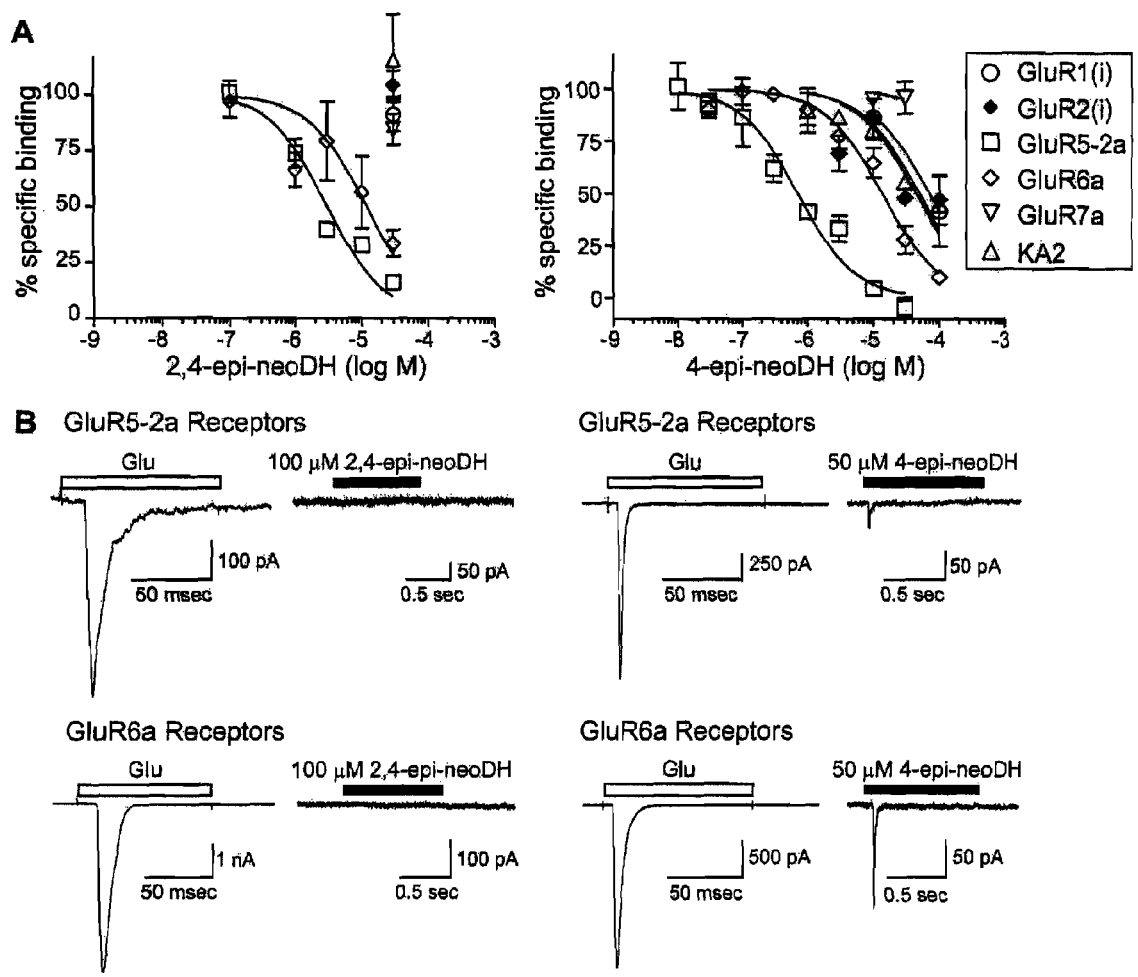
FIG. 12 illustrates that 2,4-epi-neoDH and 4-epi-neoDH maintain affinity for a subset of KAR subunits: A. Displacement of [3H]kainate and [3H]AMPA from KA and AMPARs, respectively for 2,4-epi-neoDH (left) and 4-epi-neoDH (right). 1 mM glutamate was used to determine nonspecific binding. Curves were fit with a one-site competition curve with fixed minima (0%) and maxima (100%). n=3-5 for each concentration of analog on each receptor subunit. Ki's were calculated with the Cheng-Prusoff equation using the determined IC50 values and the radioligand Kd and are in Table 3; B. 100 µM 2,4-epineoDH (1 s) fails to activate GluR5-2a or GluR6a receptors (left column). In contrast, 50 µM 4-epi-neoDH activates both GluR5-2a and GluR6a receptors (right column).

Uncontrolled chirality in the synthetic pathway for neoDH yielded two analogs of the marine toxin, 4-epi-neoDH and 2,4-epi-neoDH, in which the L-glutamate backbone in neoDH had altered stereochemistry (Sakai et al., 2001a) (FIG. 7) and therefore seemed unlikely to bind KARs with significant affinity. However, these molecules were weakly convulsant when injected i.c.v. (Shoji et al., 2006), suggesting that they might retain affinity for a subset of receptors. In binding studies, 2,4-epi-neoDH selectively displaced [3H] kainate from GluR5-2a and GluR6a subunits (Ki=2.4 μM and 7.7 μM, respectively; n=3-4) with no detectable activity on other KAR or AMPAR subunits (>100 μM, n=3-4) (Table 3, FIG. 12A). In contrast, 4-epi-neoDH bound to both GluR52a and GluR6a KAR subunits, with similar affinities relative to 2,4-epi-neoDH (Ki values of 559 nM and 6.7 μM, respectively; n=3) (FIG. 12B, Table 3), but also weakly displaced radioligand from other KA and AMPAR subunits (n=3). Neither 2,4-epineoDH nor 4-epi-neoDH bound the GluR7 receptor appreciably. Thus, these molecules exhibit distinct pharmacological profiles, and 2,4-epi-neoDH in particular appears to have a level of KAR selectivity (over AMPA receptors) not observed previously.

The pharmacological activities of the C2/C4 epimers were determined in patch-clamp assays with GluR5-2a or GluR6a KARs as well as GluR4(i) AMPA receptors. Application of 2,4-epi-neoDH (100 μM) failed to elicit detectable current in either GluR52a or GluR6a-expressing cells (n=3-5, FIG. 12C,D) and thus does not exhibit agonist activity. In contrast, a high concentration (50 μM) of 4-epi-neoDH evoked small but detectable currents from GluR5-2a and GluR6a receptors (n=3-6, FIG. 12C,D).

Figure 13:
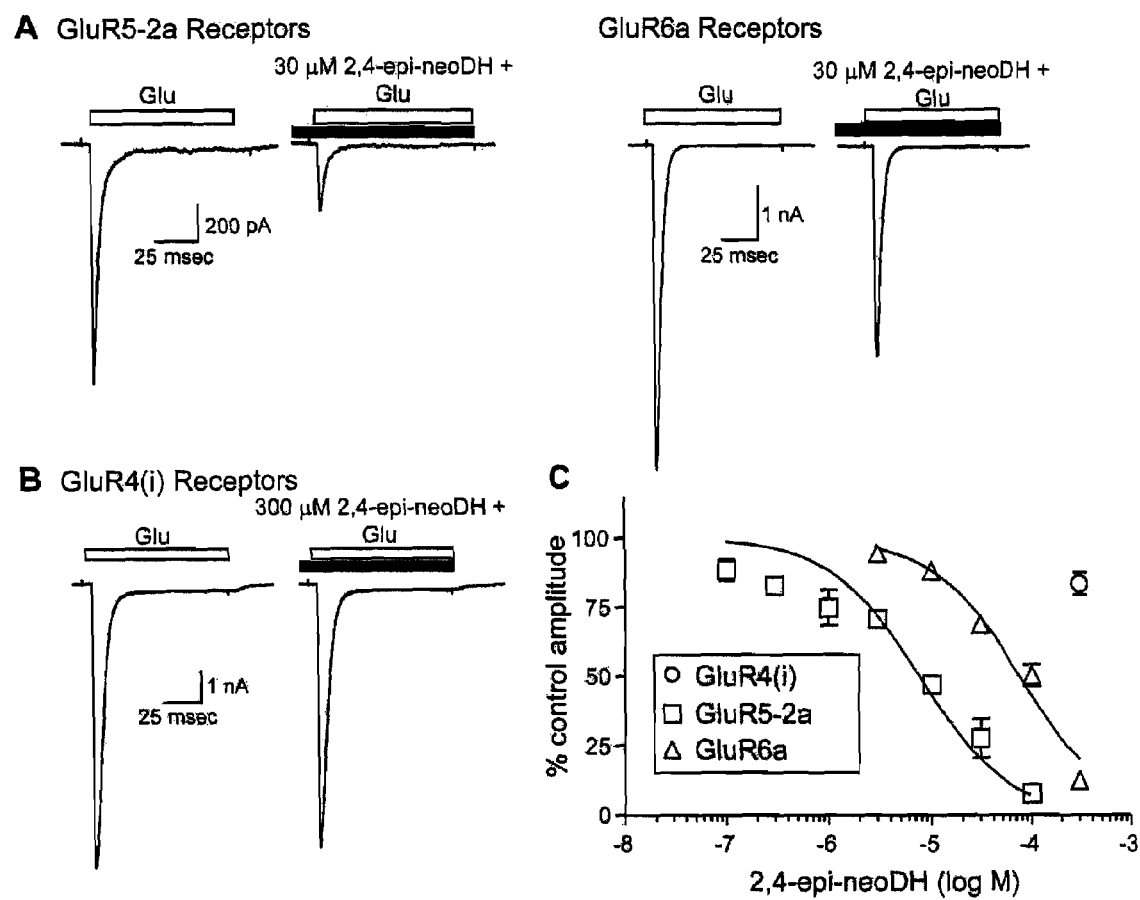
FIG. 13 illustrates that 2,4-epi-neoDH is a KAR antagonist: A. Representative traces of glutamate-evoked currents (10 mM) from GluR5-2a and GluR6a receptors before application of 30 µM 2,4-epi-neoDH; subsequent glutamate-evoked currents in the presence of the analog were attenuated; B. Currents from GluR4(i) receptors were not reduced by 300 µM 2,4-epi-neoDH; C. Inhibition-response curves for 2,4-epi-neoDH on recombinant GluR4(i), GluR5-2a, and GluR6a receptors. Logistic fits were constrained to fixed minima (0%) and maxima (100%) and IC50 values were determined to be 7.5 µM and 74 µM for GluR5-2a and GluR6a receptors, respectively. n=3-5 for each concentration.

2,4-epi-neoDH exhibited antagonist activity; this was demonstrated by applying varying concentrations of 2,4-epi-neoDH before testing with glutamate in the continued presence of the analog. 30 μM 2,4-epi-neoDH reduced glutamate-induced currents from GluR5-2a receptors by −70% while the same concentration reduced glutamate-induced currents from GluR6a receptors by −30% (FIG. 13A). In contrast, application of 300 μM 2,4-epi-neoDH failed to inhibit GluR4 (i) AMPARs (FIG. 13A). Inhibition-response analysis revealed that IC50 values for 2,4-epi-neoDH were 7.5 μM and 74 μM on GluR52a and GluR6a receptors, respectively (n=3 for each concentration, FIG. 13B). We noted that the data derived from recording of the GluR5-2a receptor was poorly fit by the single component logistic curve, particularly at the lower concentrations. This inconsistency may arise from inter-subunit or inter-dimer cooperativity in the inhibitory activity or may be an apparent artifact resulting from run-down of the GluR5-2a receptor currents. In summary, these results demonstrate that, 2,4-epi-neoDH is an antagonist (or possibly a very weak partial agonist) for these receptors.

Figure 14:
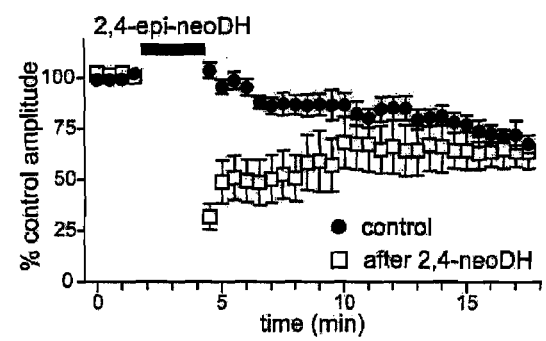
FIG. 14 illustrates that low affinity C2/C4 epimers have long lasting inhibitory effects on glutamate-evoked currents: A. The time course of recovery after application of 30 µM 2,4-epineoDH (left) and 30 µM 4-epi-neoDH (right) on GluR5-2a receptors; B. The time course of recovery after application of the analogs to GluR6a receptors. The graphs show the normalized peak amplitudes of glutamate-evoked currents before and after analog application at the indicated times (n=3-4 at each time point).
Figure 14:
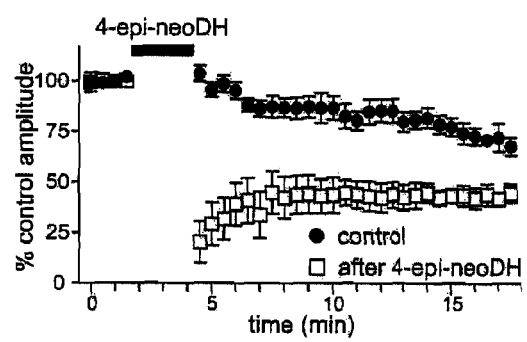
Figure 14:
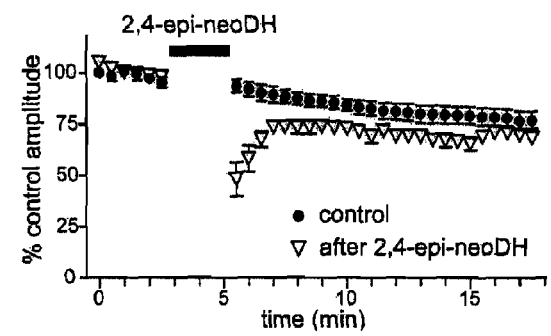
Figure 14:
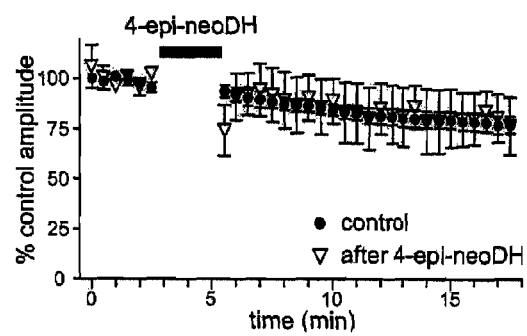

We noted the receptor desensitization induced by application of either 2,4-epi-neoDH or 4-epi-neoDH was prolonged after a brief exposure to these ligands, demonstrating that these analogs had longer-lasting interactions with the receptors than would be predicted by their relatively low binding affinities. This was evident in the attenuation of the peak current amplitudes in response to test applications of glutamate after application of the analogs. FIG. 14 compares the run-down of the receptor currents (with no analog application) to the amplitude of glutamate-evoked currents preceding and in the 13 minutes following application to either GluR5-2a (n=9, FIG. 14A) or GluR6a (n=4, FIG. 14B) receptors. Both compounds remained associated with the GluR5-2a receptor for many minutes after analog application. Recovery from desensitization is marginally more rapid after 2,4-epi-neoDH (n=3-6) compared to 4-epi-neoDH (n=3-5); the latter analog additionally stabilizes a desensitized state of the receptor, as revealed by the incomplete recovery back to control levels (within the time scale of our experiment). Conversely, current amplitudes recovered more slowly after application of 2,4-epi-neoDH to GluR6a receptors (n=3-6), and 4-epi-neoDH (n=3-4) only exhibited a transient desensitization. These observations suggest that the analogs could be useful as functional antagonists for a subpopulation of kainate receptors.

Discussion

Kainate receptors primarily subserve modulatory functions in the brain, and for that reason may represent approachable targets for therapeutic manipulation in a number of neurological diseases. Development of a wider variety of pharmacological tools that act on KARs will be particularly useful for exploring their utility as drug targets. Towards that end, here we extended our previous studies on analogs of the natural marine toxins dysiherbaine and neodysiherbaine to characterize further the structural basis for specificity and activity at KARs (Sanders et al., 2005; Sanders et al., 2006).

Our primary findings from the current study are four-fold. First, we determined that the stereochemistry of the C8 and C9 hydroxyl groups was a critical determinant of affinity for all receptor subunits except GluR5-2a, which was relatively insensitive to changes in orientation unless both hydroxyl groups were altered. Second, we found that the change in affinity for KARs observed with MSVIII-19 (8,9-dideoxy-neoDH), relative to the parent compound neoDH, is largely accounted for by loss of the C9 hydroxyl group. Unlike MSVIII-19, however, 9-deoxy-neoDH remained an agonist, which likely underlies its more potent convulsant activity (Shoji et al., 2006). Third, two new compounds, 2,4-epineoDH and 4-epi-neoDH, were found to have novel pharmacological profiles, and furthermore the former acts as a GluR5-2a- and GluR6a-selective KAR antagonist. Fourth, we observed a surprising dissociation between the relatively low binding affinity of 2,4-epi-neoDH and 4-epi-neoDH for the GluR5-2a subunit and a prolonged association in a stable, ligand-bound desensitized state in physiological studies. These results suggest that the conformational state measured in the equilibrium binding assays does not represent the highest affinity state stabilized by the compound, and that these analogs could represent effective functional antagonists at concentrations significantly lower than that required for receptor activation. In summary, our results provide several new insights into the molecular basis for specificity and selectivity of these compounds and suggest that the 2,4-epi-neoDH and 4-epi-neoDH molecules represent new templates for synthetic manipulation that could lead to novel pharmacological profiles of KAR antagonism.

Divergence in Binding Affinity and Functional Activity: What Interactions Underlie Agonism and Antagonism?

Our previous studies demonstrated that MSVIII-19, or 8,9-dideoxy-neoDH, is a high-affinity antagonist for GluR5 receptors, but MD simulations supported a relatively closed structure similar to that observed with agonists (Sanders et al., 2005; Sanders et al., 2006). Notably, the Ki of MSVIII-19 was significantly higher than its potency for inhibition of glutamate-evoked currents from GluR5 receptors (Ki=128 nM, IC50=23 nM) (Sanders et al., 2005). One of our objectives in the current study was to compare the activity of intermediate analogs that had only a single hydroxyl group removed, which we anticipated would lend insight into the unusual behavior of MSVIII-19. The binding affinity of 9-deoxy-neoDH closely matches that of MSVIII-19, as does its ability to inhibit glutamate-evoked currents by pre-desensitizing GluR5 receptors, suggesting that the pharmacological profile of MSVIII-19 for GluR5 KAR subunits results primarily from the loss of the C9 hydroxyl group. However, in functional assays 9-deoxy-neoDH acts as an agonist while MSVIII-19 is a antagonist, and it is likely that this agonist activity underlies the higher seizurogenic activity of 9-deoxyneoDH (Shoji et al., 2006). Thus, we postulate that the interaction between the C8 hydroxyl group in 9-deoxyneoDH, or more potently, the C9 hydroxyl in 8-deoxy-neoDH, and S741 in the LBD underlies the difference in agonist versus antagonist activity of these compounds. Finally, it is apparent that the high-affinity, desensitized functional state promoted by low concentrations of 9-deoxy-neoDH, for example, does not necessarily correspond to the conformation of the receptors assumed during equilibrium binding experiments, because of the divergence in binding affinity and potency of inhibition.

A similar divergence in apparent affinity and functional activity was noted for the 4-epineoDH molecule. The Ki value of ~560 nM for GluR5-2a receptors suggests that the interaction is of rather low affinity, but this is belied by the markedly long duration of inhibition of glutamate-evoked currents (FIG. 14). We conclude that the inhibitory activity exhibited by 4-epi-neoDH arises from prolonged and stable binding to the desensitized state of the receptor; a similar but significantly longer-lasting activity was first observed with the high-affinity agonist DH, which desensitizes GluR5-2a receptors irreversibly within the context of our physiological recordings (Swanson et al., 2002). In summary, the unique structures of a subset of DH, neoDH and related analogs stabilize unusually stable desensitized states in KARs (primarily GluR5) that are preceded by varying degrees of receptor activation.

Activity at GluR5 Subunits Correlates with Seizure Activity

Figure 15:
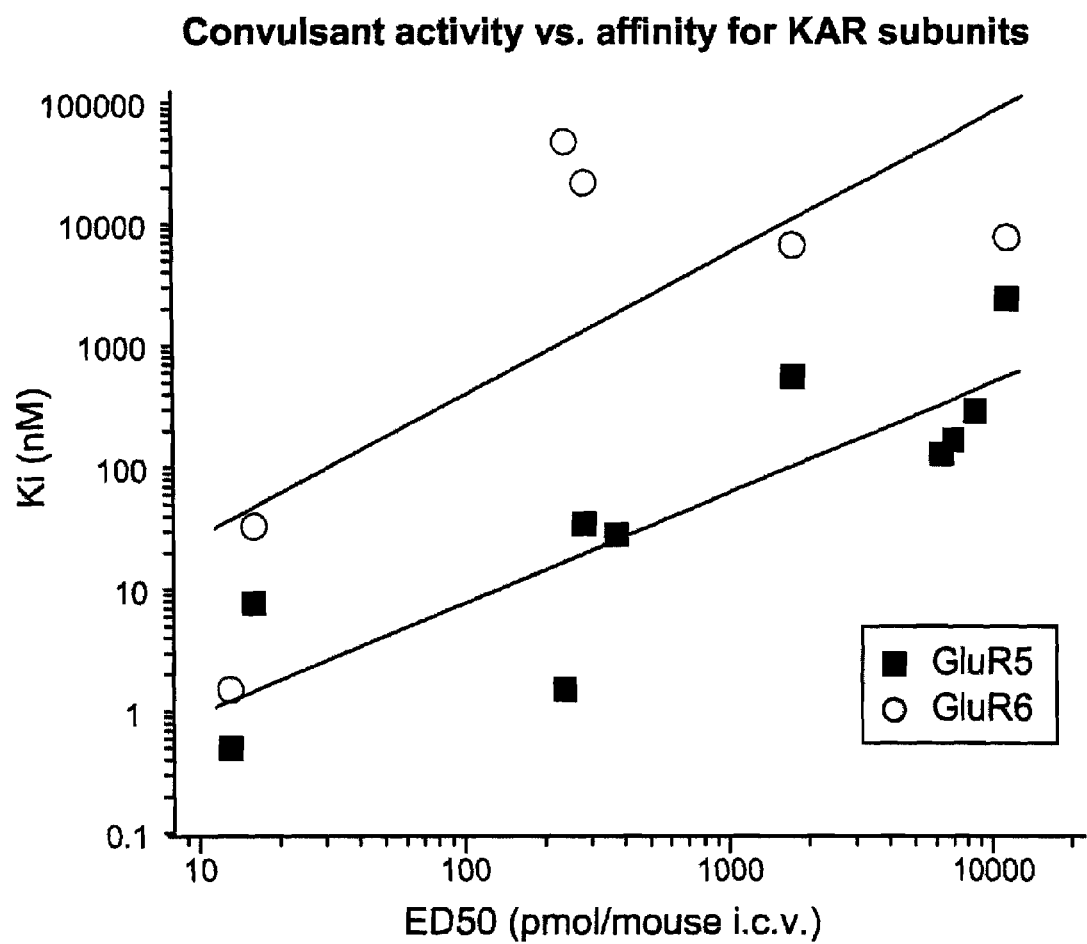
FIG. 15 illustrates that binding affinity at GluR5-2a subunits correlates with seizure activity. Linear correlation graph is plotted as Ki (nM) versus ED50 (pmol/mouse) after i.c.v. injection of the following compounds: DH (13 pmol/mouse), neoDH (16 pmol/mouse), MSVII-19 (6.3 nmol/mouse), 8-deoxy-neoDH (238 pmol/mouse), 9-deoxy-neoDH (7.1 nmol/mouse), 8epi-neoDH (283 pmol/mouse), 9-epi-neoDH (8.6 nmol/mouse), 9-F-8-epi-neoDH (374 pmol/mouse), 2,4-epi-neoDH (11.4 nmol/mouse), and 4-epi-neoDH (1.7 nmol/mouse) (Shoji et al., 2006). These data show a correlation with r=0.86, p<0.01 for binding affinity of analogs for GluR5-2a KAR subunits. A much weaker correlation between seizure activity and binding affinity for GluR6a subunits of a subset of analogs was noted (r=0.74, p=0.095); a number of the compounds could not be included in this analysis because they do not exhibit measurable affinity for this receptor subunit (i.e., MSVIII-19, 9-deoxy-neoDH, 9-epi-neoDH, and 9-F-8-epi-neoDH). Similarly, no correlation analysis was possible with GluR7a, KA2 or AMPA receptor subunits because of the absence of binding affinity.

KARs agonists are known to be potent convulsants (Ben-Ad and Cossart, 2000), and DH, the first marine toxin isolated from *Dysidea herbacea*, exhibits the most potent seizurogenic activity of any excitatory amino acid (Sakai et al., 1997). Most of the subsequent analogs of DH elicit varying degrees of convulsant behaviors; MSVIII-19, as an exception, produced sub-seizure stereotyped behavior followed by unresponsiveness (Sasaki et al., 1999; Sakai et al., 2001a). 8,9-epi-neoDH also fails to elicit convulsive behavior even at high doses, likely due to its very low affinity for KARs. Given that the analogs exhibit a range of seizure potencies and binding affinities, we attempted to determine if these two parameters were strongly correlated. As shown in FIG. 15, we found that the affinity for GluR5-2a KAR subunits and convulsant activity of a range of compounds, as indicated by ED50 values upon i.c.v. injection in mice, were highly correlated ($r=0.89$, $p<0.01$). In contrast, a weaker correlation was observed between seizure activity and binding affinity for GluR6a subunits ($r=0.74$, $p=0.095$), and this lower correlation is likely an overestimate given that many analogs could not be included in the analysis because they showed no affinity for the GluR6a subunit. No apparent correlations were possible with GluR7a, KA2 or AMPA receptor binding because these subunits in large part did not interact with the analogs. This relationship strongly supports the hypothesis that activation of GluR5-containing receptors, which in the hippocampus predominantly reside on interneurons, underlies convulsant activity. Efficacy as GluR5 agonists likely further contributes to the seizurogenic potency of the analogs characterized within this study, particularly since the analogs show varied functional behavior with some acting as very weak partial agonists (i.e. 9-epi-neoDH) and others acting as full agonists or highly efficacious partial agonists (i.e. 8-deoxy-neoDH). This could be the case for the C2/C4 epimer analogs, which have generally similar binding profiles but notable differences in their potency for seizure induction. 2,4epi-neoDH binds GluR5-2a receptors with a Ki of 2.4 µM and has an ED50 of 11.4 nmol/mouse, while 4-epi-neoDH binds GluR5-2a receptors with slightly higher affinity (Ki=559 nM) but has an ED50 that is >6-fold lower than that of 2,4-epi-neoDH (ED50 of 4-epi-neoDH=1.7 nmol/mouse). The most notable difference between these two analogs is their efficacy as agonists, in that 4-epi-neoDH elicits large currents from both GluR5-2a and GluR6a receptors while 2,4-epi-neoDH fails to activate GluR5 or GluR6 receptors, even at 100 µM, and rather acts as a antagonist. Thus, GluR5-2a agonist efficacy likely is an important factor, in addition to binding affinity for receptor subunits, in the seizure potency of these analogs.

This correlation supports the development of GluR5-selective antagonists as potential anticonvulsant compounds. The efficacy of this strategy was demonstrated in studies in which two GluR5 subunit-selective antagonists, LY377770 and LY382884, prevented induction and maintenance of seizure activity in multiple models of epilepsy (Smolders et al., 2002). More recently, aberrant KAR signaling was shown to contribute to hyperexcitability following seizurogenesis, and this activity was attenuated by desensitization of KARs (Epsztein et al., 2005); the subunit composition of the receptors involved in this process, however, were not identified pharmacologically. In some respects, the strong correlation with GluR5 binding was a surprise, because a number of studies suggest that GluR6-containing receptors are the predominant targets of KAR agonists that lead to convulsions. In particular, gene targeting of the GluR6 subunit attenuates susceptibility to kainate-induced seizures (Mulle et al., 1998; Fisahn et al., 2004). It is possible that the specificity of the neoDH analogs for GluR5 receptors elicits seizurogenesis through distinct mechanisms than kainate, which is relatively nonselective and will activate all kainate and AMPA receptors (depending on the concentration). In any case, our results further demonstrate that selective activation of GluR5-containing receptors produces seizures. It will be of interest to determine how this induction process occurs within the brain.

In summary, this characterization of neoDH analogs offers further insight into the determinants of activity and subunit selectivity for KAR subunits. Slight structural modifications of the parent molecule generated compounds with novel pharmacological profiles. In particular, 2,4-epi-neoDH is the first compound to act as a functional antagonist selective for GluR5 and GluR6-containing receptors without concurrent activity on AMPA receptors. We suggest that this compound will serve as a useful tool for further study of KARs in synaptic physiology and pathological conditions.

LIST OF REFERENCES FOR EXAMPLE 2

Alt A, Weiss B, Ornstein P L, Gleason S D, Bleakman D, Stratford R E, Jr. and Witkin J M (2007) Anxiolytic-like effects through a GLU(K5) kainate receptor mechanism. Neuropharmacology 52:1482-1487.

Ben-Ari Y and Cossart R (2000) Kainate, a double agent that generates seizures: two decades of progress. Trends Neurosci 23:580-587.

Christensen J K, Varming T, Ahring P K, Jorgensen T D and Nielsen E O (2004) In Vitro Characterization of 5-Carboxyl-2,4-di-benzamidobenzoic Acid (NS3763), a Noncompetitive Antagonist of GLUK5 Receptors. J Pharmacol Exp Ther 309:10031010.

Dolman N P, More J C, Alt A, Knauss J L, Pentikäinen O T, Glasser C R, Bleakman D, Mayer M L, Collingridge G L and Jane D E (2007) Synthesis and pharmacological characterization of N3-substituted willardiine derivatives: role of the substituent at the 5-position of the uracil ring in the development of highly potent and selective GLUK5 kainate receptor antagonists. J Med Chem 50:1558-1570.

Epsztein J, Represa A, Jorquera I, Ben-Ari Y and Crepe V (2005) Recurrent mossy fibers establish aberrant kainate receptor-operated synapses on granule cells from epileptic rats. J Neurosci 25:8229-8239.

Filla S A, Winter M A, Johnson K W, Bleakman D, Bell M G, Bleisch T J, Castano A M, Clemens-Smith A, del Prado M, Dieckman D K, Dominguez E, Escribano A, Ho K H, Hudziak K J, Katofiasc M A, Martinez-Perez J A, Mateo A, Mathes B M, Mattiuz E L, Ogden A M, Phebus L A, Stack D R, Stratford R E and Ornstein P L (2002) Ethyl (3S,4aR,6S,8aR)-6-(4-ethoxycar-bonylimidazol-1-ylmethyl)decahydroiso-quinoline-3-carboxylic ester: a prodrug of a GluR5 kainate receptor antagonist active in two animal models of acute migraine. J Med Chem 45:4383-4386.

Fisahn A, Contractor A, Traub R D, Buhl E H, Heinemann S F and McBain C J (2004) Distinct roles for the kainate receptor subunits GluR5 and GluR6 in kainate-induced hippocampal gamma oscillations. J Neurosci 24:9658-9668.

Frisch M J, Trucks G W, Schlegel H B, Scuseria G E, Robb M A, Cheeseman J R, Montgomery J, J. A., Vreven T, Kudin K N, Burant J C, Millam J M, Lyengar S S, Tomasi J, Barone V, Mennucci B, Cossi M, Scalmani G, Rega N, Petersson G A, Nakatsuji H, Hada M, Ehara M, Toyota K, Fukuda R, Hasegawa J, Ishida M, Nakajima T, Honda Y, Kitao O, Nakai H, Klene M, Li X, Knox J E, Hratchian H P, Cross J B, Bakken V, Adamo C, Jaramillo J, Gomperts R, Stratmann R E, Yazyev O, Austin A J, Cammi R, Pomelli C, Ochterski J W, Ayala P Y, Morokuma K, Voth G A, Salvador P, Dannenberg J J, Zakrzewski V G, Dapprich S, Daniels A D, Strain M C, Farkas 0, Malick D K, Rabuck A D, Raghavachari K, Foresman J B, Ortiz J V, Cui Q, Baboul A G, Clifford S, Cioslowski J, Stefanov B B, Liu G, Liashenko A, Piskorz P, Komaromi I, Martin R L, Fox D J, Keith T, Al-Laham M A, Peng C Y, Nanayakkara A, Challacombe M, Gill P M W, Johnson B, Chen W, Wong M W, Gonzalez C and Pople J A (2004) Gaussian 03, in, Gaussian, Inc., Wallingford Conn.

Herb A, Burnashev N, Werner P, Sakmann B, Wisden W and Seeburg P H (1992) The KA-2 subunit of excitatory amino acid receptors shows widespread expression in brain and forms ion channels with distantly related subunits. Neuron 8:775-785.

Hollmann M and Heinemann S (1994) Cloned glutamate receptors. Annu. Rev. Neurosci. 17:31-108.

Jones G, Willett P, Glen R C, Leach A R and Taylor R (1997) Development and validation of a genetic algorithm for flexible docking. J Mol Biol 267:727-748.

Kew J N and Kemp J A (2005) Ionotropic and metabotropic glutamate receptor structure and pharmacology. Psychopharmacology (Bert) 179:4-29.

Lerma J (2006) Kainate receptor physiology. Curr Opin Pharmacol 6:89-97.

Lerma J, Patemain A V, Rodriguez-Moreno A and Lopez-Garcia J C (2001) Molecular physiology of kainate receptors. Physiol Rev 81:971-998.

Mayer M L (2005) Crystal Structures of the GluR5 and GluR6 Ligand Binding Cores: Molecular Mechanisms Underlying Kainate Receptor Selectivity. Neuron 45:539-552.

Mulle C, Sailer A, Perez-Otafio I, Dickinson-Anson H, Castillo P E, Bureau I, Maron C, Gage F H, Mann J R, Bettler B and Heinemann S F (1998) Altered synaptic physiology and reduced susceptibility to kainate-induced seizures in GluR6-deficient mice. Nature 392:601-605.

Nanao M H, Green T, Stem-Bach Y, Heinemann S F and Choe S (2005) Structure of the kainate receptor subunit GluR6 agonist-binding domain complexed with domoic acid. Proc Natl Acad Sci USA 102:1708-1713.

Naur P, Vestergaard B, Skov L K, Egebjerg J, Gajhede M and Kastrup J S (2005) Crystal structure of the kainate receptor GluR5 ligand-binding core in complex with (S)-glutamate. FEBS Letters 579:1154-1160.

Paternain A V, Vicente A, Nielsen E O and Lerma J (1996) Comparative antagonism of kainate-activated kainate and AMPA receptors in hippocampal neurons. Eur J Neurosci 8:2129-2136.

Pentikäinen U, Pentikäinen O T and Mulholland A J (2007) Cooperative symmetric to asymmetric conformational transition of the apo-form of scavenger decapping enzyme revealed by simulations. Proteins: Structure, Function, and Bioinformatics In press.

Pentikäinen U, Settimo L, Johnson M S and Pentikäinen O T (2006) Subtype selectivity and flexibility of ionotropic glutamate receptors upon antagonist ligand binding. Org Biomol Chem 4:1058-1070.

Phillips J C, Braun R, Wang W, Gumbart J, Tajkhorshid E, VIIIa E, Chipot C, Skeel R D, Kale L and Schulten K (2005) Scalable molecular dynamics with NAMD. Journal of Computational Chemistry 26:1781-1802.

Pinheiro P and Mulle C (2006) Kainate receptors. Cell Tissue Res 326:457-482.

Sakai R, Kamiya H, Murata M and Shimamoto K (1997) Dysiherbaine: a new neurotoxic amino acid from the Micronesian marine sponge *Dysidea herbacea*. Journal of the American Chemical Society 119:4112-4116.

Sakai R, Koike T, Sasaki M, Shimamoto K, Oiwa C, Yano A, Suzuki K, Tachibana K and Kamiya H (2001a) Isolation, structure determination, and synthesis of neodysiherbaine A, a new excitatory amino acid from a marine sponge. Org Lett 3:1479-1482.

Sakai R, Swanson G T, Shimamoto K, Green T, Contractor A, Ghetti A, Tamura-Horikawa Y, Oiwa C and Kamiya H (2001b) Pharmacological properties of the potent epileptogenic amino acid dysiherbaine, a novel glutamate receptor agonist isolated from the marine sponge *Dysidea herbacea*. JPET 296:650-658.

Sanders J M, Ito K, Settimo L, Pentikäinen O T, Shoji M, Sasaki M, Johnson M S, Sakai R and Swanson G T (2005) Divergent pharmacological activity of novel marine-derived excitatory amino acids on glutamate receptors. J Pharmacol Exp Ther 314:1068-1078.

Sanders J M, Pentikäinen O T, Settimo L, Pentikäinen U, Shoji M, Sasaki M, Sakai R, Johnson M S and Swanson G T (2006) Determination of binding site residues responsible for the subunit selectivity of novel marine-derived compounds on kainate receptors. Mol Pharmacol 69:1849-1860.

Sasaki M, Maruyama T, Sakai R and Tachibana K (1999) Synthesis and biological activity of dysiherbaine model compound. Tetrahedron Letters 40:3195-3198.

Shoji M, Akiyama N, Tsubone K, Lash L L, Sanders J M, Swanson G T, Sakai R, Shimamoto K, Oikawa M and Sasaki M (2006) Total synthesis and biological evaluation of neodysiherbaine A and analogues. J Org Chem 71:5208-5220.

Smolders I, Bortolotto Z A, Clarke V R, Warre R, Khan G M, O'Neill M J, Ornstein P L, Bleakman D, Ogden A, Weiss B, Stables J P, Ho K H, Ebinger G, Collingridge G L, Lodge D and Michotte Y (2002) Antagonists of GLU(K5)-containing kainate receptors prevent pilocarpine-induced limbic seizures. Nat Neurosci 5:796-804.

Swanson G T, Gereau R W, IV, Green T and Heinemann S F (1997) Identification of amino acid residues that control functional behavior in GluR5 and GluR6 kainate receptors. Neuron 19:913-926.

Swanson G T, Green T, Sakai R, Contractor A, Che W, Kamiya H and Heinemann S F (2002) Differential activation of individual subunits in heteromeric kainate receptors. Neuron 34:589-598.

Valgeirsson J, Nielsen E O, Peters D, Mathiesen C, Kristensen A S and Madsen U (2004) Bioisosteric modifications of 2-arylureidobenzoic acids: selective noncompetitive antagonists for the homomeric kainate receptor subtype GluR5. J Med Chem 47:69486957.

Valgeirsson J, Nielsen E O, Peters D, Varming T, Mathiesen C, Kristensen A S and Madsen U (2003) 2-arylureidobenzoic acids: selective noncompetitive antagonists for the homomeric kainate receptor subtype GluR5. J Med Chem 46:5834-5843.

Weiss B, Alt A, Ogden A M, Gates M, Dieckman D K, Clemens-Smith A, Ho K H, Jarvie K, Rizkalla G, Wright R A, Calligaro D O, Schoepp D, Mattiuz E L, Stratford R E, Johnson B, Saihoff C, Katofiasc M, Phebus L A, Schenck K, Cohen M, Filla S A, Ornstein P L, Johnson K W and Bleakman D (2006) Pharmacological characterization of the competitive GLUK5 receptor antagonist decahydroisoquinoline LY466195 in vitro and in vivo. J Pharmacol Exp Ther 318:772-781.

Werner P, Voigt M, Keinanen K, Wisden W and Seeburg P H (1991) Cloning of a putative high-affinity kainate receptor expressed predominantly in hippocampal CA3 cells. Nature 351:742-744.

We claim:

1. A pharmaceutical composition comprising:
   (a) a compound having the formula

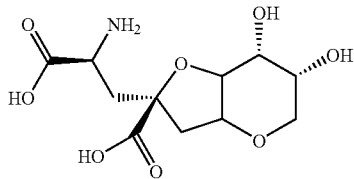

and
   (b) one or more pharmaceutically acceptable carriers, diluents, or excipients.

2. The composition of claim 1, wherein the composition is suitable for administration to a human.

3. The composition of claim 1, wherein the composition is suitable for oral administration.

4. The composition of claim 1, wherein the composition is suitable for transdermal administration.

* * * * *

UNITED STATES PATENT AND TRADEMARK OFFICE
CERTIFICATE OF CORRECTION

PATENT NO.       : 7,973,075 B2
APPLICATION NO.  : 12/243281
DATED            : July 5, 2011
INVENTOR(S)      : Geoffrey T. Swanson et al.

It is certified that error appears in the above-identified patent and that said Letters Patent is hereby corrected as shown below:

Column 1, Lines 12-18

Please replace the paragraph following the header, "STATEMENT REGARDING FEDERALLY SPONSORED RESEARCH OR DEVELOPMENT" with the following rewritten paragraph:

This invention was made with government support under grant number NS044322 awarded by the National Institutes of Health. The government has certain rights in the invention.

Signed and Sealed this
Third Day of July, 2012

David J. Kappos
*Director of the United States Patent and Trademark Office*